United States Patent
Hagen et al.

(10) Patent No.: US 10,120,136 B2
(45) Date of Patent: Nov. 6, 2018

(54) INDEXING SIGNAL DETECTION MODULE

(71) Applicant: GEN-PROBE INCORPORATED, San Diego, CA (US)

(72) Inventors: Norbert D. Hagen, Carlsbad, CA (US); David Opalsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 15/287,358

(22) Filed: Oct. 6, 2016

(65) Prior Publication Data
US 2017/0023743 A1    Jan. 26, 2017

Related U.S. Application Data

(62) Division of application No. 14/200,460, filed on Mar. 7, 2014, now Pat. No. 9,465,161.
(Continued)

(51) Int. Cl.
*G02B 6/04* (2006.01)
*G02B 6/36* (2006.01)
(Continued)

(52) U.S. Cl.
CPC ......... *G02B 6/3668* (2013.01); *G01N 21/253* (2013.01); *G01N 21/6452* (2013.01);
(Continued)

(58) Field of Classification Search
CPC .... G02B 6/3668; G02B 6/368; G02B 6/4296; G02B 27/09; G01N 2021/6484; G01N 2201/0826
See application file for complete search history.

(56) References Cited

U.S. PATENT DOCUMENTS

| | | | | |
|---|---|---|---|---|
| 4,039,250 A | * | 8/1977 | Gaertner | G02B 6/06 385/115 |
| 4,106,231 A | * | 8/1978 | MacNiel | G09F 9/305 340/815.42 |

(Continued)

FOREIGN PATENT DOCUMENTS

| | | |
|---|---|---|
| CN | 102533539 A | 7/2012 |
| EP | 0902271 A2 | 3/1999 |

(Continued)

OTHER PUBLICATIONS

De Silva, D. et al. "Monitoring hybridization during polymerase chain reaction", Journal of Chromatography B: Biomedical Applications, Apr. 1, 2000 (Apr. 1, 2000), pp. 3-13, vol. 741, No. 1, Elsevier Science Publishers, NL.
(Continued)

*Primary Examiner* — Thanh Luu
(74) *Attorney, Agent, or Firm* — Charles B. Cappellari; David L. Devermoe; Richard Wydeven

(57) ABSTRACT

An indexing signal detection module is configured to index one or more signal detectors past each of a plurality of sources of detectable signal emissions to detect or measure a signal emitted by each source. A plurality of signal transmission conduits transmit signal emitted by the sources from a first end of each conduit to a second end of each conduit where the signal may be detected by a signal detector. A conduit reformatter is configured to secure the first ends of the respective signal transmission conduits in a first spatial arrangement corresponding to a spatial arrangement of the signal emission sources and to secure the second ends of the respective signal transmission conduits in a second spatial arrangement different from the first spatial arrangement.

13 Claims, 17 Drawing Sheets

Related U.S. Application Data

(60) Provisional application No. 61/782,340, filed on Mar. 14, 2013.

(51) Int. Cl.

| | |
|---|---|
| *G02B 6/06* | (2006.01) |
| *G02B 6/08* | (2006.01) |
| *G01N 21/25* | (2006.01) |
| *G01N 21/64* | (2006.01) |
| *G02B 6/42* | (2006.01) |

(52) U.S. Cl.
CPC ............... *G02B 6/06* (2013.01); *G02B 6/08* (2013.01); *G02B 6/3672* (2013.01); *G02B 6/4214* (2013.01); *G02B 6/4246* (2013.01); *G02B 6/4269* (2013.01); *G01N 2021/6484* (2013.01)

(56) References Cited

U.S. PATENT DOCUMENTS

| | | | |
|---|---|---|---|
| 4,144,452 A | 3/1979 | Harte | |
| 4,542,987 A | 9/1985 | Hirschfeld | |
| 5,589,351 A | 12/1996 | Harootunian | |
| 6,141,366 A * | 10/2000 | Yoneda ............... | G02B 6/4249 372/50.1 |
| 6,191,852 B1 | 2/2001 | Paffhausen et al. | |
| 7,081,226 B1 | 7/2006 | Witter et al. | |
| 9,465,161 B2 | 10/2016 | Hagen et al. | |
| 2002/0037526 A1 | 3/2002 | Yashiro et al. | |
| 2005/0134527 A1* | 6/2005 | Ouderkirk ............ | A61C 19/004 345/32 |
| 2005/0239197 A1 | 10/2005 | Katerkamp et al. | |
| 2005/0279949 A1 | 12/2005 | Oldham et al. | |
| 2007/0161876 A1 | 7/2007 | Bambot et al. | |
| 2008/0248586 A1 | 10/2008 | Tajima | |
| 2009/0068747 A1 | 3/2009 | Iten | |
| 2012/0190034 A1 | 7/2012 | Tajima | |
| 2012/0295249 A1 | 11/2012 | Cherubini et al. | |

FOREIGN PATENT DOCUMENTS

| | | |
|---|---|---|
| EP | 0640828 B1 | 5/2000 |
| EP | 1087222 A2 | 3/2001 |
| JP | 11-241947 A | 9/1999 |
| JP | 11-313698 A | 11/1999 |
| JP | 2001-091463 A | 4/2002 |
| JP | 2002-098696 A | 4/2002 |
| JP | 2004-144839 A | 10/2002 |
| JP | 2005-516596 A | 6/2005 |
| JP | 2008-519266 A | 6/2008 |
| JP | 2008-173127 A | 7/2008 |
| JP | 2010-117712 A | 10/2009 |
| JP | 2012-047719 A | 3/2012 |
| WO | 2011-016509 A1 | 8/2010 |

OTHER PUBLICATIONS

Sanford, Lindsay N. et al. "Monitoring temperature with fluorescence during real-time PCR and melting analysis", Analytical Biochemistry, Mar. 1, 2013 (Mar. 1, 2013), pp. 26-33, vol. 434, No. 1, Elsevier Inc.
PCT, International Search Report, International Application No. PCT/US2014/021820, dated Nov. 12, 2014.
PCT Written Opinion, International Application No. PCT/US14/021820, dated Nov. 12, 2014.
PCT International Preliminary Report on Patentability, International Application No. PCT/US14/021820, dated Sep. 15, 2015.
APO, Patent Examination Report No. 1, Australian Patent Application No. 2013202788, dated Feb. 21, 2014.
APO, Patent Examination Report No. 2, Australian Patent Application No. 2013202788, dated May 29, 2015.
APO, Notice of Allowance, Australian Patent Application No. 2013202788, dated Sep. 17, 2015.
SIPO, Office Action No. 3, Chinese Patent Application No. 201480015045.4, dated Jul. 17, 2018.
JPO, Official Action, Japanese Patent Application No. 2016-500855, dated Feb. 6, 2018.
APO, Patent Examination Report No. 1, Australian Patent Application No. 2015275317, dated Jul. 22, 2016.
APO, Patent Examination Report No. 2, Australian Patent Application No. 2015275317, dated May 19, 2017.
APO, Patent Examination Report No. 3, Australian Patent Application No. 2015275317, dated Jun. 30, 2017.
APO, Patent Examination Report No. 4, Australian Patent Application No. 2015275317, dated Jul. 27, 2017.
APO, Patent Examination Report No. 1, Australian Patent Application No. 2017208207, dated Mar. 21, 2018.
SIPO, Office Action No. 1, Chinese Patent Application No. 201480015045.4, dated Feb. 14, 2017.
SIPO, Search Report, Chinese Patent Application No. 201480015045.4, dated Feb. 14, 2017.
SIPO, Office Action No. 2, Chinese Patent Application No. 201480015045.4, dated Nov. 16, 2017.
EPO, Patent Examination Report, European Patent Application No. 14715169.0, dated Mar. 6, 2017.
USPTO, Notice of Allowance, U.S. Appl. No. 14/200,460, dated Jun. 10, 2016.

\* cited by examiner

| Interface Position | Reformatter Position |
|---|---|
| T1 | F21 |
| T2 | F20 |
| T3 | F19 |
| T4 | F18 |
| T5 | F17 |
| T6 | F26 |
| T7 | F25 |
| T8 | F16 |
| T9 | F14 |
| T10 | F13 |
| T11 | F27 |
| T12 | F24 |
| T13 | F23 |
| T14 | F12 |
| T15 | F11 |
| T16 | F28 |
| T17 | F32 |
| T18 | F6 |
| T19 | F9 |
| T20 | F10 |
| T21 | F30 |
| T22 | F31 |
| T23 | F4 |
| T24 | F5 |
| T25 | F7 |
| T26 | F33 |
| T27 | F34 |
| T28 | F35 |
| T29 | F2 |
| T30 | F3 |

FIG. 10

INDEXING SIGNAL DETECTION MODULE

CROSS REFERENCE TO RELATED APPLICATIONS

This application is a division of U.S. patent application Ser. No. 14/200,460, filed Mar. 7, 2014, which claims the benefit under 35 U.S.C. § 119(e) of the filing date of U.S. provisional Patent Application Ser. No. 61/782,340, filed Mar. 14, 2013, the content of each of which is hereby incorporated by reference herein in their entirety.

FIELD

This disclosure relates to an apparatus for detecting a signal emitted by each of a plurality of potential signal emission sources by indexing one or more signal detectors with respect to the signal emission sources to sequentially detect a signal from each signal emission source. The disclosure further relates to an apparatus for transmitting a signal emission from each of a plurality potential signal emission sources between first and second ends of signal transmission conduits, wherein the first ends of the signal transmission conduits are disposed in a first spatial arrangement, and the second ends of the signal transmission conduits are disposed in a second spatial arrangement different from the first spatial arrangement.

BACKGROUND

None of the references described or referred to herein are admitted to be prior art to the claimed invention.

Diagnostic assays are widely used in clinical diagnosis and health science research to detect or quantify the presence or amount of biological antigens, cell or genetic abnormalities, disease states, and disease-associated pathogens or genetic mutations in an organism or biological sample. Where a diagnostic assay permits quantification, practitioners may be better able to calculate the extent of infection or disease and to determine the state of a disease over time. Diagnostic assays are frequently focused on the detection of chemicals, proteins or polysaccharides antigens, antibodies, nucleic acids, amino acids, biopolymers, cells, or tissue of interest. A variety of assays may be employed to detect these diagnostic indicators.

Nucleic acid-based assays, in particular, generally include multiple steps leading to the detection or quantification of one or more target nucleic acid sequences in a sample. The targeted nucleic acid sequences are often specific to an identifiable group of proteins, cells, tissues, organisms, or viruses, where the group is defined by at least one shared sequence of nucleic acid that is common to members of the group and is specific to that group in the sample being assayed. A variety of nucleic acid-based detection methods are fully described by Kohne, U.S. Pat. No. 4,851,330, and Hogan, U.S. Pat. No. 5,541,308.

Detection of a targeted nucleic acid sequence frequently requires the use of a probe comprising a nucleic acid molecule having a nucleotide base sequence that is substantially complementary to at least a portion of the targeted sequence or its complement. Under selective assay conditions, the probe will hybridize to the targeted sequence or its complement in a manner permitting a practitioner to detect the presence of the targeted sequence in a sample. Techniques of effective probe preparation are known in the art. In general, however, effective probes are designed to prevent non-specific hybridization with itself or any nucleic acid molecule that will interfere with detecting the presence of the targeted sequence. Probes may include, for example, a label capable of detection, where the label is, for example, a radiolabel, a fluorophore or fluorescent dye, biotin, an enzyme, a chemiluminescent compound, or another type of detectable signal known in the art.

To detect different nucleic acids of interest in a single assay, different probes configured to hybridize to different nucleic acids, each of which may provide detectably different signals can be used. For example, different probes configured to hybridize to different targets can be formulated with fluorophores that fluoresce at a predetermined wavelength when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices constructed and arranged to periodically measure signal emissions during the amplification process, and with different signal detecting devices being configured to generate excitation signals of different wavelengths and to measure emission signals of different wavelengths.

Because the probe hybridizes to the targeted sequence or its complement in a manner permitting detection of a signal indicating the presence of the targeted sequence in a sample, the strength of the signal is proportional to the amount of target sequence or its complement that is present. Accordingly, by periodically measuring, during an amplification process, a signal indicative of the presence of amplicon, the growth of amplicon overtime can be detected. Based on the data collected during this "real-time" monitoring of the amplification process, the amount of the target nucleic acid that was originally in the sample can be ascertained. Exemplary systems and methods for real time detection and for processing real time data to ascertain nucleic acid levels are described, for example, in Lair, et al., U.S. Pat. No. 7,932,081, "Signal measuring system for conducting real-time amplification assays.".

Challenges may arise, however, when measuring emission signals during an amplification process or other process. The target sequence or its complement, or other emission signal source, may be contained in a receptacle that is held within an incubator or other processing module that is fully or partially enclosed and for which access by a signal detector to the receptacle or other source for measuring the emission signal may not be practical. Moreover, for space utilization efficiencies and/or other efficiencies (such as thermal efficiencies), the receptacles or other emission signal sources may positioned in a spatial arrangement for which it is not efficient or practical to place a signal detector in operative position to measure the emission signals. For example, a plurality of receptacles or emission signal sources may be arranged in a rectangular arrangement whereby the receptacles are closely spaced in multiple rows of two or more receptacles each. In such a spatial arrangement, it may not be practical or efficient to provide a signal detector for each receptacle position or to move a signal detector with respect to the receptacle positions to sequentially measure signal emissions from each of the receptacles.

SUMMARY

Aspects of the disclosure are embodied in an apparatus for detecting a signal emission from each of a plurality of potential signal emission sources. The apparatus comprises a plurality of signal transmission conduits, a conduit reformatter, one or more signal detectors, and a signal detector carrier. The signal transmission conduits correspond in number to the number of signal emission sources. Each signal transmission conduit is associated with at least one of the signal emission sources and is configured to transmit a signal emitted by the associated signal emission source between a first end and a second end thereof. The conduit reformatter is constructed and arranged to secure the first ends of the respective signal transmission conduits in a first spatial arrangement corresponding to a spatial arrangement of the signal emission sources, such that the first end of each signal transmission conduit is positioned to receive an emission signal emitted by an associated signal emission source, and to secure the second ends of the respective signal transmission conduits in a second spatial arrangement different from the first spatial arrangement. The signal detectors are configured to detect a signal emitted by each signal emission source. The signal detector carrier is configured to carry at least a portion of the one or more signal detectors and to move at least a portion of each signal detector in a path that sequentially places the signal detector in signal detecting positions with respect to the second ends of the signal transmission conduits arranged in the second spatial arrangement.

According to further aspects of the disclosure, the signal emission is an optical signal and the signal transmission conduits comprise optical fibers.

According to further aspects of the disclosure, the first spatial arrangement is rectangular and comprises two or more rows, each row including two or more of the first ends of the signal transmission conduits.

According to further aspects of the disclosure, the second spatial arrangement comprises one or more circles, whereby the second ends of a plurality of signal transmission conduits are positioned about the circumference of a circle.

According to further aspects of the disclosure, the second spatial arrangement comprises one or more bundles whereby the second ends of a plurality of signal transmission conduits are collected in a bundle wherein the second ends of the transmission fibers in the bundle are in close proximity to each other.

According to further aspects of the disclosure, the signal detector carrier comprises a carousel configured to move at least a portion of the one or more signal detectors in a path corresponding to the one or more circles of the second spatial arrangement.

According to further aspects of the disclosure, the conduit reformatter comprises a reformatter frame comprising an interface plate configured to secure the first ends of the respective signal transmission conduits in the first spatial arrangement, a base configured to secure the first ends of the respective signal transmission conduits in the second spatial arrangement, and a side structure connecting the interface plate to the base at spaced-apart positions with respect to each other.

According to further aspects of the disclosure, the apparatus further comprises heat dissipating fins extending from the interface plate.

According to further aspects of the disclosure, the apparatus further comprises a signal coupling element operatively disposed with respect to the first end of each signal transmission conduit.

According to further aspects of the disclosure, the signal detector carrier is constructed and arranged to be rotatable about an axis of rotation so as to move each of the one or more signal detectors in a circular path, and the apparatus further comprises a detector carrier drive operatively associated with the signal detector carrier. The detector carrier drive comprises a motor, a drive pulley coupled to or part of the signal detector carrier such that rotation of the drive pulley causes a corresponding rotation of the signal detector carrier, and a belt operatively coupling the motor to the drive pulley.

According to further aspects of the disclosure, the detector carrier drive further comprises a home position detector configured to detect a rotational position of the detector carrier.

According to further aspects of the disclosure, the signal detector carrier is configured to rotate about an axis of rotation, and the apparatus further comprises a rotary connector transmitting power and/or data between the one more signal detectors carried on the signal detector carrier and a non-rotating data processor and/or power source.

According to further aspects of the disclosure, the rotary connector comprises a slip ring connector.

According to further aspects of the disclosure, the each signal emission source comprises a substance that emits light of a predetermined emission wavelength when subjected to an excitation light of a predetermined excitation wavelength, and the signal detector is configured to generate an excitation light of the predetermined excitation wavelength and detect light of the predetermined emission wavelength.

According to further aspects of the disclosure, the apparatus comprises more than one signal detector, each configured to generate an excitation light of a different predetermined excitation wavelength and to detect light of a different predetermined emission wavelength.

According to further aspects of the disclosure, each of the signal emission sources is in optical communication with a single signal transmission conduit.

According to further aspects of the disclosure, each of the plurality of signal transmission conduits transmits both an excitation and an emission signal.

According to further aspects of the disclosure, the each signal detector comprises an excitation source carried on the signal detector carrier and configured to generate an excitation signal, excitation optics components carried on the signal detector carrier and configured to direct an excitation signal from the excitation source to the second end of a signal transmission conduit when the signal detector is in a signal detecting position with respect to the second end of the transmission conduit, emission optics components carried on the signal detector carrier and configured to direct an emission signal transmitted by a signal transmission conduit when the signal detector is in a signal detecting position with respect to the second end of the transmission conduit, and an emission detector configured to detect an emission signal directed by the emission optics components from the second end of the transmission conduit to the emission detector when the signal detector is in a signal detecting position with respect to the second end of the transmission conduit.

According to further aspects of the disclosure, the emission detector is carried on the signal detector carrier.

According to further aspects of the disclosure, the emission detector comprises a photodiode.

According to further aspects of the disclosure, the emission detector is fixed and disposed adjacent to the signal detector carrier.

According to further aspects of the disclosure, the emission detector comprises a camera.

According to further aspects of the disclosure, the emission detector is associated with at least one excitation source and is configured to detect an emission signal transmitted by a single transmission conduit.

According to further aspects of the disclosure, the signal detector carrier is configured to selectively place each set of excitation optics components into operative association with the emission detector, and the emission detector is configured to detect an emission signal transmitted by all single transmission conduits simultaneously.

Further aspects of the disclosure are embodied in an apparatus for transmitting a signal emission from each of a plurality of potential signal emission sources. The apparatus comprises a plurality of signal transmission conduits and a conduit reformatter. Each signal transmission conduit is configured to transmit a signal emitted by one or more of the signal emission sources between a first end and a second end thereof. The conduit reformatter is constructed and arranged to secure the first ends of the respective signal transmission conduits in a first spatial arrangement corresponding to a spatial arrangement of the signal emission sources, such that the first end of each signal transmission conduit is positioned to receive an emission signal emitted by one or more of the signal emission sources, and to secure the second ends of the respective signal transmission conduits in a second spatial arrangement different from the first spatial arrangement.

According to further aspects of the disclosure, the signal emission is an optical signal and the signal transmission conduits comprise optical fibers.

According to further aspects of the disclosure, the first spatial arrangement is rectangular and comprises two or more rows, each row including two or more of the first ends of the signal transmission conduits.

According to further aspects of the disclosure, the second spatial arrangement comprises one or more circles, whereby the second ends of a plurality of signal transmission conduits are positioned about the circumference of a circle.

According to further aspects of the disclosure, the second spatial arrangement comprises one or more bundles whereby the second ends of a plurality of signal transmission conduits are collected in a bundle wherein the second ends of the transmission fibers in the bundle are in close proximity to each other.

According to further aspects of the disclosure, the conduit reformatter comprises a reformatter frame comprising an interface plate configured to secure the first ends of the respective signal transmission conduits in the first spatial arrangement, a base configured to secure the first ends of the respective signal transmission conduits in the second spatial arrangement, and a side structure connecting the interface plate to the base at spaced-apart positions with respect to each other.

According to further aspects of the disclosure, the apparatus further comprises heat dissipating fins extending from the interface plate.

According to further aspects of the disclosure, the apparatus further comprises a signal coupling element operatively disposed with respect to the first end of each signal transmission conduit.

Further aspects of the disclosure are embodied in a method of measuring at least one time-varying signal emission from the contents of a receptacle while the contents are subject to repeated cycles of temperature variations. The method comprises measuring the signal emission from the contents of the receptacle at repeating intervals of time and recording the signal emission measurement and a time stamp at each interval, recording the temperature to which the contents of the receptacle are subjected at repeating intervals of time and recording the time stamp at each interval, and synchronizing the signal emission to a specific temperature by comparing the time stamps of the signal emission measurements to time stamps of the recorded temperature corresponding to the specific temperature.

Further aspects of the disclosure are embodied in an apparatus for detecting an emission signal from each of a plurality of emission signal sources, wherein each emission signal is excited by an excitation signal. The apparatus comprises one or more excitation sources configured to generate an excitation signal that is directed at an emission signal source, one or more emission detectors, each emission detector being associated with at least one excitation source and being configured to detect an emission signal emitted by an excitation source and excited by the excitation signal generated by the associated excitation signal source, and a carrier configured to move the one or more excitation sources and the one or more emission detectors relative to the emission signal sources to thereby index each emission detector and associated excitation source past each of the emission signal sources.

According to further aspects of the disclosure, the each emission signal source comprises a substance that emits light of a predetermined emission wavelength when subjected to an excitation signal of a predetermined excitation wavelength and each excitation source is configured to generate an excitation light of the predetermined excitation wavelength and each associated emission detector is configured to detect light of the predetermined emission wavelength.

According to further aspects of the disclosure, the apparatus comprises more than one excitation source, each configured to generate an excitation light of a different predetermined excitation wavelength, and more than one associated emission detector, each configured to detect light of a different predetermined emission wavelength.

According to further aspects of the disclosure, the carrier is configured to rotate about an axis of rotation and move each emission detector and associated excitation source in a circular path.

Other features and characteristics of the present disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the present disclosure. In the drawings, common reference numbers indicate identical or functionally similar elements.

FIG. 10 is a table showing mapping between the interface fiber positions and the baseplate fiber positions shown in FIGS. 8 and 9.

DETAILED DESCRIPTION

Figure 1:
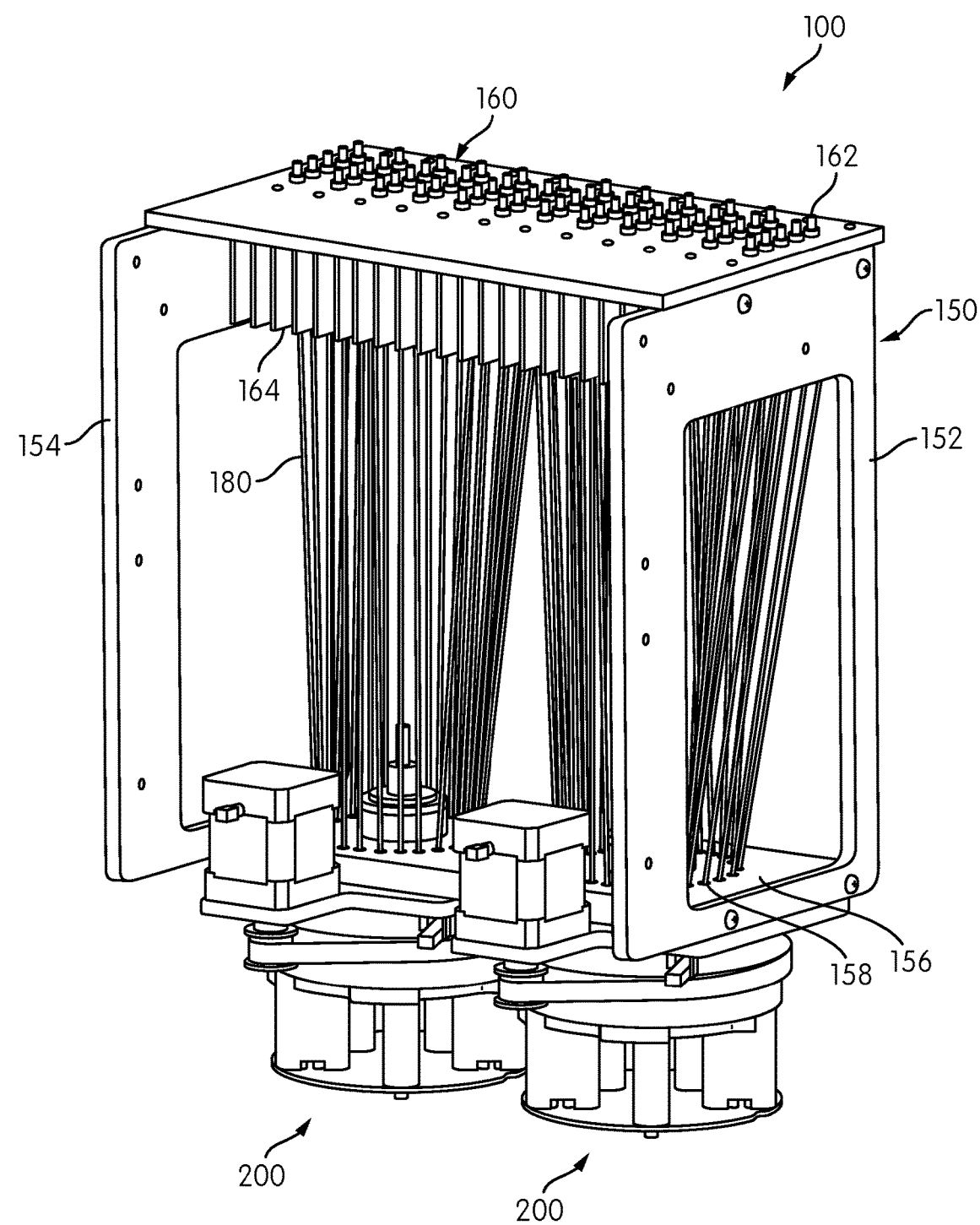
FIG. 1 is a perspective view of a signal detection module embodying aspects of the present disclosure.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Nucleic Acid Diagnostic Assays

Aspects of the present disclosure involve apparatus and procedures for transmitting and/or measuring signals emitted by potential emission signal sources and can be used in conjunction with nucleic acid diagnostic assays, including "real-time" amplification assays and "end-point" amplification assays.

There are many established procedures in use for amplifying nucleic acids, including the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), strand displacement amplification (SDA), (see, e.g., Walker, "Strand Displacement Amplification," U.S. Pat. No. 5,455,166), and loop-mediated isothermal amplification (see, e.g., Notomi et al., "Process for Synthesizing Nucleic Acid," U.S. Pat. No. 6,410,278). A review of several amplification procedures currently in use, including PCR and TMA, is provided in HELEN H. LEE ET AL., NUCLEIC ACID AMPLIFICATION TECHNOLOGIES (1997).

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations. Exemplary systems and methods for performing real-time amplification assays are described in U.S. Pat. No. 7,897,337, entitled "Methods for Performing Multi-Formatted Assays," and in U.S. Pat. No. 8,008,066, entitled, "System for performing multi-formatted assays."

In addition to implementation of embodiments of the disclosure in conjunction with real-time amplification assays, embodiments of the disclosure may also be implemented in conjunction with end point amplification assays. In end-point amplification assays, the presence of amplification products containing the target sequence or its complement is determined at the conclusion of an amplification procedure. Exemplary systems and methods for end-point detection are described in U.S. Pat. No. 6,335,166, entitled "Automated Process For Isolating and Amplifying a Target Nucleic Acid Sequence." In contrast, in "real-time" amplification assays, the amount of amplification products containing the target sequence or its complement is determined during an amplification procedure. In the real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

For real-time amplification assays, the probes are, in certain embodiments, unimolecular, self-hybridizing probes having a pair of interacting labels that interact and thereby emit different signals, depending on whether the probes are in a self-hybridized state or hybridized to the target sequence or its complement. See, e.g., Diamond et al., "Displacement Polynucleotide Assay Method and Polynucleotide Complex Reagent Therefor," U.S. Pat. No. 4,766,062; Tyagi et al., "Detectably Labeled Dual Conformation Oligonucleotide Probes, Assays and Kits," U.S. Pat. No. 5,925,517; Tyagi et al., "Nucleic Acid Detection Probes Having Non-FRET Fluorescence Quenching and Kits and Assays Including Such Probes," U.S. Pat. No. 6,150,097; and Becker et al., "Molecular Torches," U.S. Pat. No. 6,361,945. Other probes are known, including complementary, bimolecular probes, probes labeled with an intercalating dye and the use of intercalating dyes to distinguish between single-stranded and double-stranded nucleic acids. See, e.g., Morrison, "Competitive Homogenous Assay," U.S. Pat. No. 5,928,862; Higuchi, "Homogenous Methods for Nucleic Acid Amplification and Detection," U.S. Pat. No. 5,994,056; and Yokoyama et al., "Method for Assaying Nucleic Acid," U.S. Pat. No. 6,541,205. Examples of interacting labels include enzyme/substrate, enzyme/cofactor, luminescent/quencher, luminescent/adduct, dye dimers and Forrester energy transfer pairs. Methods and materials for joining interacting labels to probes for optimal signal differentiation are described in the above-cited references. A variety of different labeled probes and probing mechanisms are known in the art, including those where the probe does not hybridize to the target sequence. See, e.g., U.S. Pat. No. 5,846,717 and PCT Publication No. 2012096523. The embodiments of the present disclosure operate regardless of the particular labeling scheme utilized provided the moiety to be detected can be excited by a particular wavelength of light and emits a distinguishable emission spectra.

In an exemplary real-time amplification assay, the interacting labels include a fluorescent moiety, or other emission moiety, and a quencher moiety, such as, for example, 4-(4-dimethylaminophenylazo)benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to a nucleic acid present in the sample, the fluorescent and quencher moieties are separated from each other and light energy emitted by the fluorescent moiety can be detected. Fluorescent moieties having different and distinguishable excitation and emission wavelengths are often combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties. In another embodiment, different fluorescent moieties having the same excitation wavelength, but different and distinguishable emission wavelengths are combined with different probes. The presence and amount of target nucleic acids associated with each probe can be determined by exposing the sample to a specific wavelength light energy and the light emission from the sample at the different wavelengths corresponding to the different fluorescent moieties is measured.

In one example of a multiplex, real-time amplification assay, the following may be added to a sample prior to initiating the amplification reaction: a first probe having a quencher moiety and a first fluorescent dye (having an excitation wavelength $\lambda_{ex1}$ and emission wavelength $\lambda_{em1}$) joined to its 5' and 3' ends and having specificity for a nucleic acid sequence derived from HCV; a second probe having a quencher moiety and a second fluorescent dye (having an excitation wavelength $\lambda_{ex2}$ and emission wavelength $\lambda_{em2}$) joined to its 5' and 3' ends and having specificity for a nucleic acid sequence derived from HIV Type 1 (HIV-1); and a third probe having a quencher moiety and a third fluorescent dye (having an excitation wavelength $\lambda_{ex3}$ and emission wavelength $\lambda_{em3}$) joined to its 5' and 3' ends and having specificity for a nucleic acid sequence derived from West Nile virus (WNV). After combining the probes in a sample with amplification reagents, the samples can be periodically and alternately exposed to excitation light at wavelengths $\lambda_{ex1}$, $\lambda_{ex2}$, and $\lambda_{ex3}$, and then measured for emission light at wavelengths $\lambda_{em1}$, $\lambda_{em2}$, and $\lambda_{em3}$, to detect the presence (or absence) and amount of all three viruses in the single sample. The components of an amplification reagent will depend on the assay to be performed, but will generally contain at least one amplification oligonucleotide, such as a primer, a promoter-primer, and/or a promoter oligonucleotide, nucleoside triphosphates, and cofactors, such as magnesium ions, in a suitable buffer.

Where an amplification procedure is used to increase the amount of target sequence, or its complement, present in a sample before detection can occur, it is desirable to include a "control" to ensure that amplification has taken place. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus calling into question the results from that assay. Alternatively, failure to detect emission light may be due to failure or deteriorated mechanical and/or electrical performance of an instrument (described below) for detecting the emission light.

Apparatus and procedures embodying aspects of the disclosure may be used a variety of nucleic acid amplification procedures, including in conjunction with real-time PCR, which requires accurate/rapid thermocycling between denaturation (~95° C.), annealing (~55° C.), and synthesis (~72° C.) temperatures. For this purpose, receptacles containing a reaction mixture that is to be subject to PCR are held in a thermocycler configured to effect temperature cycling between the denaturation, annealing, and synthesis phases. Emission signal monitoring (e.g., of fluorescence) of the contents of the receptacles held in the thermocycler occurs at one or many color wavelengths during each temperature cycle between 95° C., 55° C., and synthesis 72° C. PCR components include; for example, a forward and a reverse amplification oligonucleotides, and a labeled poly or oligonucleotide probe. During one exemplary PCR procedure, nucleic acid amplification oligonucleotides hybridize to opposite strands of a target nucleic acid and are oriented with their 3' ends facing each other so that synthesis by a polymerization enzyme such as a polymerase extends across the segment of nucleic acid between them. While the probe is intact, the proximity of the quencher dye quenches the fluorescence of the reporter dye. During amplification if the target sequence is present, the fluorogenic probe anneals downstream from one of the amplification oligonucleotide sites and is cleaved by the 5' nuclease activity of the polymerization enzyme during amplification oligonucleotide extension. The cleavage of the probe separates the reporter dye from the quencher dye, thus rendering detectable the reporter dye signal and, eventually, removing the probe from the target strand, allowing amplification oligonucleotide extension to continue to the end of the template strand.

One round of PCR synthesis will result in new strands of indeterminate length which, like the parental strands, can hybridize to the amplification oligonucleotides upon denaturation and annealing. These products accumulate arithmetically with each subsequence cycle of denaturation, annealing to amplification oligonucleotides, and synthesis. The second cycle of denaturation, annealing, and synthesis produces two single-stranded products that together compose a discrete double-stranded product which comprises the length between the amplification oligonucleotide ends. Each strand of this discrete product is complementary to one of the two amplification oligonucleotides and can therefore participate as a template in subsequent cycles. The amount of this product doubles with every subsequent cycle of synthesis, denaturation and annealing. This accumulates exponentially so that 30 cycles should result in a $2^{28}$-fold (270 million-fold) amplification of the discrete product.

Signal Detection Module/Fiber Reformatter

Detection, and, optionally, measurement, of emission signals from emission signal sources, such as receptacles containing reaction materials undergoing amplification as described above can be performed in accordance with aspects of the present disclosure with a signal detection module. A signal detection module embodying aspects of the present disclosure is indicated by reference number 100 in FIG. 1. The signal detection module includes an upright reformatter frame 150. Two signal detector heads 200 are attached to a lower end of the reformatter frame 150 and an interface plate 160 is attached to an upper end of the reformatter frame 150. In general, the reformatter frame includes sides 152, 154 which, in the illustrated embodiment, comprise generally vertical columns, and a base 156 within which are formed a plurality of fiber-positioning holes 158. Note that the designation of the reformatter frame 150 as being upright or the sides 152, 154 as being vertical is merely to provide a convenient reference with respect to the orientation of the signal detection module 100 as shown in FIG. 1, and such terms of orientation are not intended to be limiting. Accordingly, the signal detection module 100 could be oriented at any angle, including vertical or horizontal, or any angle therebetween. The reformatter frame has a variety of purposes, including organizing and arranging a plurality of optical transmission fibers 180 between an excitation/emission area and a detection area in an optimum optical pathway orientation. In particular embodiments the reformatter also provides for controlled orientation of a plurality of optical transmission fibers 180 between the fins of a heat sink to a detection area.

Signal transmission conduits, such as optical transmission fibers 180 extend between the interface plate 160 and the base 156 of the reformatter frame 150. In the present context, an optical transmission fiber, or optical fiber, comprises a flexible, transparent rod made of glass (silica) or plastic that functions as a waveguide, or light pipe, to transmit light between the two ends of the fiber. Optical fibers typically include a transparent core surrounded by an opaque or transparent cladding material having a lower index of refraction than the core material. A light transmission is maintained within the core by total internal reflection. Each optical fiber may comprise a single fiber having a single fiber core, or each fiber may comprise a fiber bundle of two or more fibers. Fiber bundlers may be preferred if a tight bend radius is required for the transmission fiber 180. In certain embodiments it may be preferable to provide an optical fiber cladding that is resistant to the effects of high heat indexes in that the optical transmission properties of the fiber are maintained in the presence of heat indexes well-above room temperature.

In one aspect of the disclosure, the reformatter frame is constructed and arranged to reconfigure the relative spatial arrangements of the fibers 180 from their first ends to their second ends so as to rearrange the transmission fibers 180 into a spatial arrangement in which they can be more efficiently interrogated by a signal measuring device to measure a signal transmitted therethrough. In the context of this description, the first end of the fiber 180 corresponds to the end of the fiber closest to the signal emission source is being measured, and the second end of the fiber corresponds to the end of the fiber closest to the signal detector. This is merely a convenient terminology for distinguishing one end of the transmission fiber 180 from another end of the transmission fiber 180. Otherwise, the designation of the ends of the fibers as being a first end or a second end is arbitrary.

The first ends of the transmission fibers 180 are attached to the interface plate 160, for example extending into or through openings formed through the interface plate 160. Signal coupling elements 162, e.g., ferrules, may be provided in each of the openings formed in the interface plate 160 for securely attaching each optical transmission fiber 180 to the interface plate 160. Although not shown in FIG. 1, each opening formed in the interface plate 160 may be in signal transmission communication with an emission signal source. In one embodiment, a signal emission source may comprise a receptacle containing the contents of a chemical or biological assay. In the case of optical emission signals, the receptacles may be positioned and held so as to optically isolate each receptacle from the surrounding receptacles. In addition, as noted above, the receptacles may be held within an incubator device located in optical communication with the interface plate 160, configured to alter the temperature of receptacles or maintain the receptacles at a specified temperature. In such an application, it may be desirable that the interface plate 160 is formed of a suitably heat-conducting material, such as aluminum or copper, and that the interface plate 160 further include heat dissipating fins 164 formed on one side of the interface plate 160 for dissipating heat from the interface plate 160 by convection. Also, coupling elements (ferrules) 162 may be thermally insulating to insulate the transmission fibers 180 from the heat of the receptacles held within the incubator. Suitable insulating materials include Ultem (polyethylene ketone (PEEK)).

In the embodiment illustrated in FIG. 1, the transmission fibers 180 are attached to the interface plate 160 in a rectangular configuration comprising a plurality of rows, each row having one or more transmission fibers 180. As shown in the illustrated embodiment, in an application in which the interface plate 160 includes heat dissipating fins 164, the transmission fibers 180 may extend between adjacent fins 164 into an associated opening formed in the interface plate 160. The illustrated embodiment includes twelve rows of five transmission fibers 180 each, for a total of sixty transmission fibers that can be employed for interrogating up to sixty individual emission sources, such as reaction receptacles containing reaction materials therein. Each row of transmission fibers 180 may be disposed between a pair of adjacent heat-dissipating fins 164.

The second ends of the transmission fibers 180 are connected to the base 156 of the reformatter frame 150, for example, by being aligned with or inserted into or through fiber-positioning holes 158. The fiber-positioning holes 158 are in a spatial arrangement that is different from the spatial arrangement fiber-receiving holes formed in the interface plate 160 and are in a position that can be more efficiently interrogated by one or more signal detectors. In the illustrated embodiment, each of the fiber position holes 158 is arranged in a circle, FIG. 1 exemplifies two such arrangements, each circle accommodating a plurality of the transmission fibers 180 extending from the interface plate 160. Other spatial arrangements are contemplated, including, two or more concentric circles, one or more open rectangles, one or more ovals, etc.

The length of the fiber reformatter 150 is defined by the distance between the base 156 and the interface plate 160 and is selected by balancing two, sometimes competing considerations. On the one hand, to make the signal detection module 100 as compact as possible, the smallest possible length of the fiber reformatter 150 is desired. On the other hand, because the flexibility of the transmission fibers 180 may be limited, a longer fiber reformatter 150 will make it easier to bend each transmission fiber 180 when reformatting the fiber from its position within the fiber arrangement in the interface plate 160 to its position in the fiber arrangement in the base 156 of the fiber reformatter 150. In one embodiment, using thirty fibers having a diameter of 1.5 mm, a fiber reformatter having a length of 200-300 mm was found to be suitable. In other embodiments, plastic fibers having a diameter of 1.5 mm and a length of 165 mm+/−10 mm were used.

Figure 2:
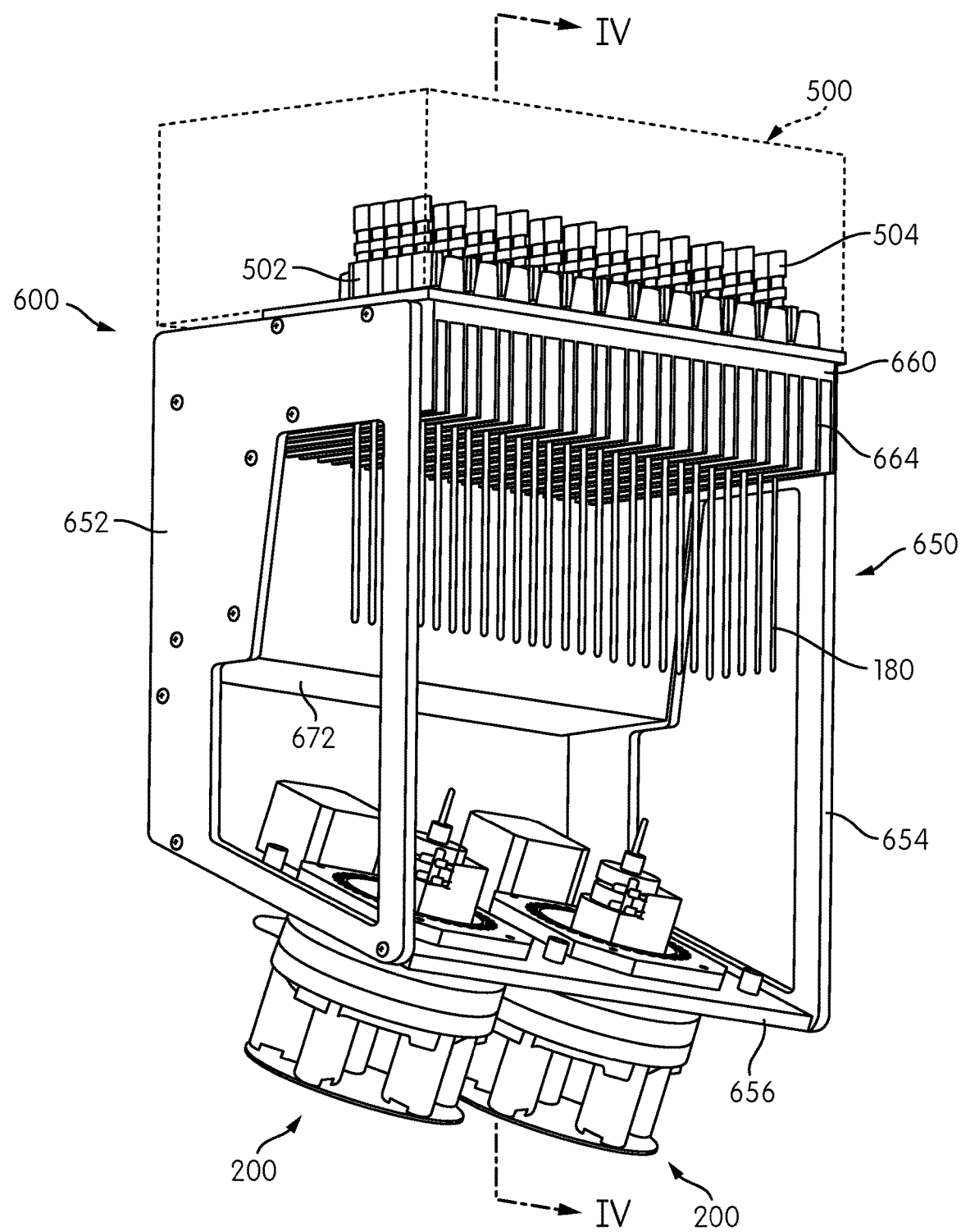
FIG. 2 is a front perspective view of a signal detection module embodying aspects of the present disclosure and according to an alternate embodiment.
Figure 3:
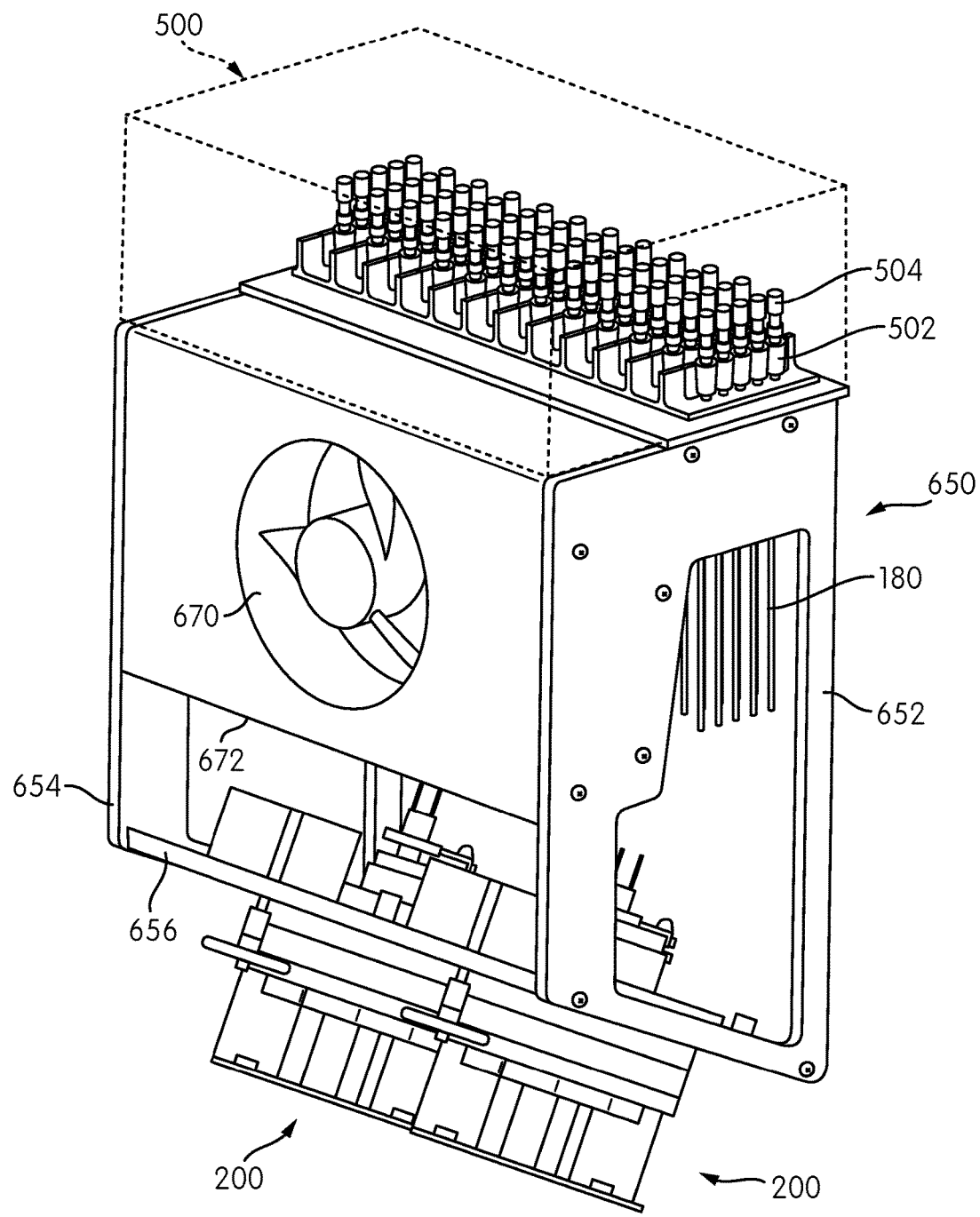
FIG. 3 is a rear perspective view of the signal detection module shown in FIG. 2.
Figure 4:
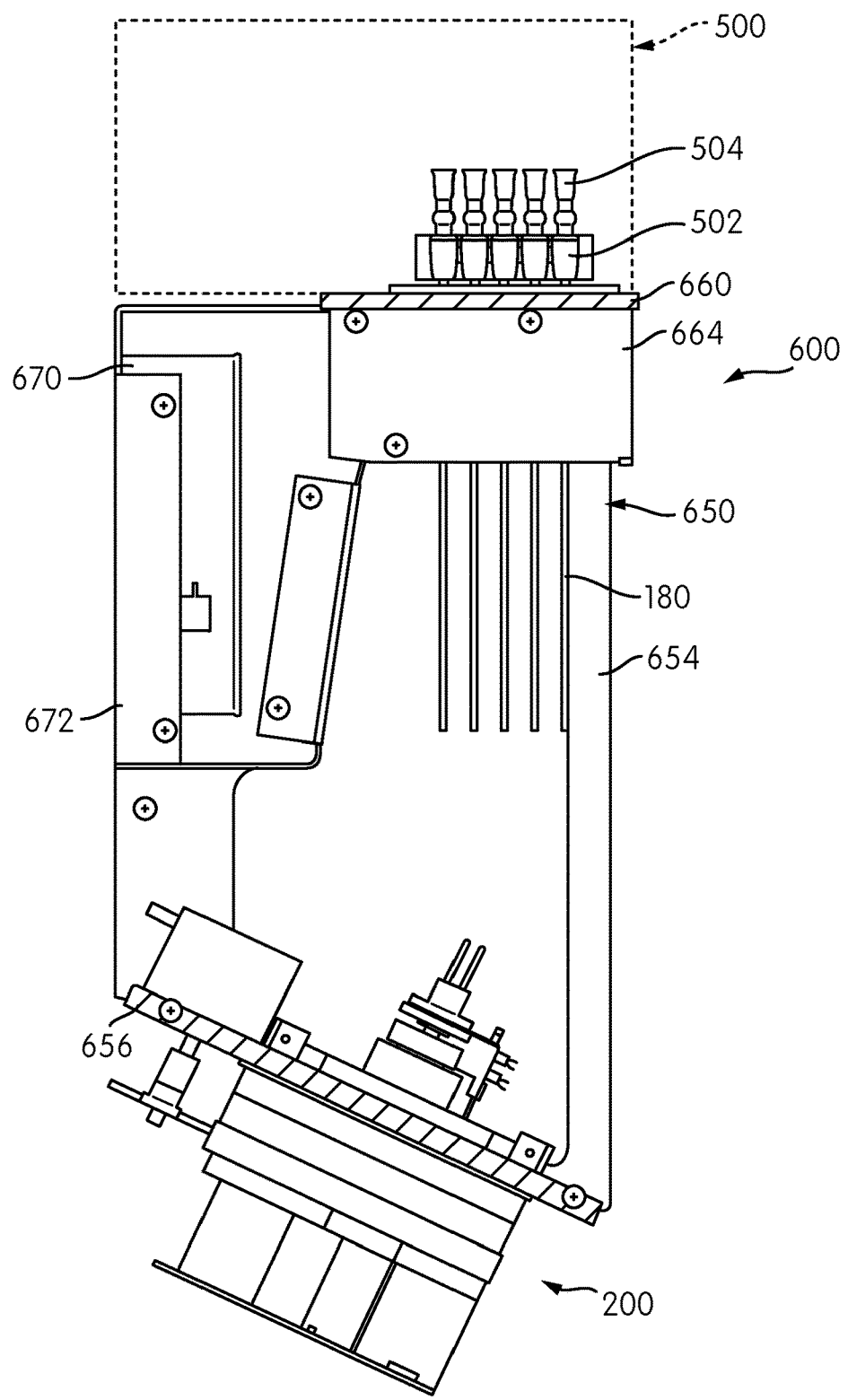
FIG. 4 is a transverse cross-section of the signal detection module along the line IV-IV in FIG. 2.

A somewhat modified embodiment of the signal detection module embodying aspects of the present disclosure is represented by reference number 600 in FIGS. 2, 3, and 4. The signal detection module 600 includes a reformatter frame 650 that includes sides 652, 654 and a base 656. An interface plate 660 is attached to one end of the reformatter frame 650, and two signal detector heads 200 are attached to the base 656 at an opposite end of the reformatter frame 650. As opposed to the embodiment show in FIG. 1, in which the base 156 of the reformatter frame 150 forms a generally orthogonal angle with respect to the sides 152,154 of the reformatter frame 150 such that the base 156 is generally parallel to the interface plate 160, the reformatter frame 650 of signal detection module 600 is configured such that the base 656 is at an acute angle with respect to the sides 652, 654 so that the base 656 is not parallel to the interface plate 660.

Transmission fibers 180 extend from a first end thereof connected to the interface plate 660 in a first spatial arrangement to a second end thereof connected to the base 656 in a second spatial arrangement. As with the embodiment shown in FIG. 1, the transmission fibers 180 are reformatted from a generally rectangular configuration attached to the interface plate 660 into two circular arrangements, each accommodating half of the transmission fibers 180, attached to the base 656.

As also shown in FIGS. 2 to 4, a processing module 500, such as an incubator, including a plurality of receptacle holders 502, each configured to hold one or more receptacles 504, is positioned above the interface plate 660. In the illustrated embodiment, the receptacle holders 502 are constructed and arranged to hold sixty receptacles 504 arranged in twelve rows of five receptacles 504 each. In one embodiment, processing module 500 may be an incubator, and each receptacle holder 502 may be constructed and arranged to impart thermal energy to the receptacles 504 held thereby to change and/or maintain the temperature of the contents of each receptacle 504. In one embodiment, processing module 500 comprises an incubator as disclosed in Application Ser. No. 61/677,976, filed on Jul. 31, 2012, to the extent published in U.S. Patent Application Publication No. 2014-0038192, which claims priority therefrom.

For applications in which heat dissipation from the interface plate 660 is necessary or desirable, such as when the processing module 500 disposed on the interface plate 660 comprises an incubator or other heat-generating device, heat dissipating fins 664 may be provided on the interface plate 660. To augment heat dissipation via the heat dissipating fins 664, the signal detection module 600 may include a fan 670 disposed within a fan housing 672 mounted to the reformatter frame 650. Fan 670 is constructed and arranged to generate air flow over the heat dissipating fins 664 to enhance the convective heat dissipation from the fins 664.

Figure 6:
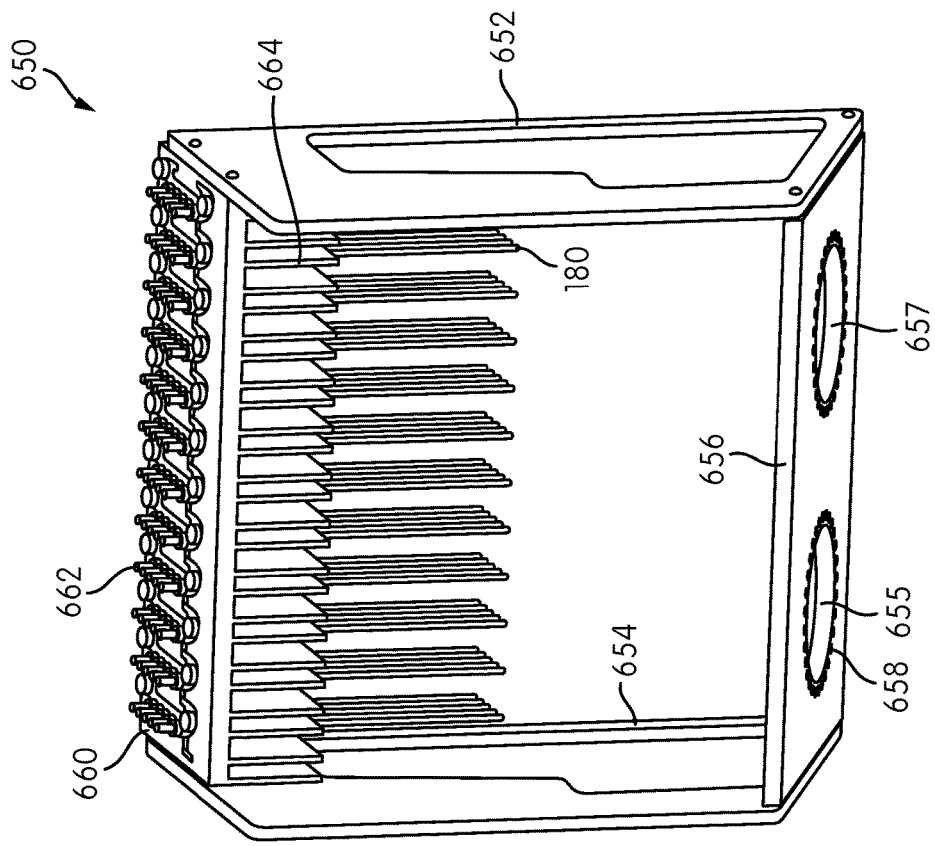
FIG. 6 is a rear perspective view of a fiber reformatter and interface plate shown in FIG. 5.
Figure 5:
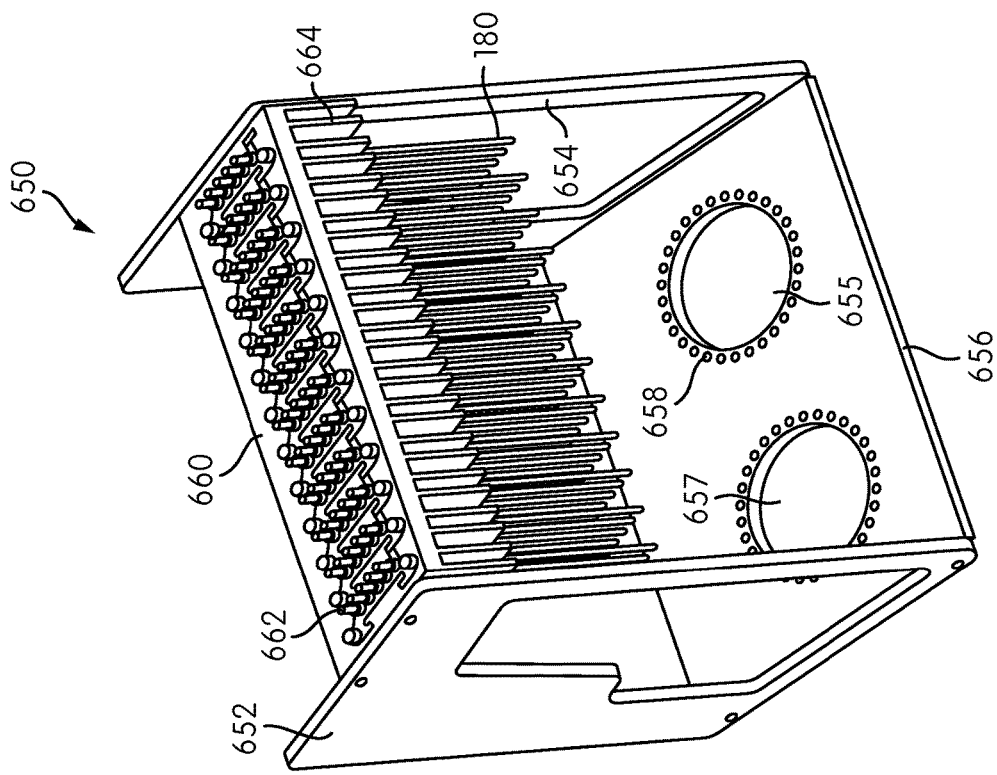
FIG. 5 is a front perspective view of a fiber reformatter and interface plate of the signal detection module shown in FIGS. 2-4.

FIGS. 5 and 6 show front and rear, respectively, perspective views of the fiber reformatter frame 650 of the signal detection module 600 shown in FIGS. 2-4. The signal detector heads 200, the processing module 500, the fan 670, and the fan housing 672 are not shown in FIGS. 5 and 6. The reformatter frame 650 includes sides 652, 654, a base 656 attached to one end of the sides 652, 654, and an interface plate 660 attached to an opposite end of the sides 652, 654. Signal coupling elements 662 are attached to each of the fiber-receiving openings formed in the interface plate 660. As explained above, coupling elements 662, which may comprise ferrules, are constructed and arranged to couple a signal, e.g., an optic signal, from the corresponding transmission fiber 180 to an object to be interrogated, such as the contents of a receptacle, and/or couple an optical emission from the object into the transmission fiber 180.

The base 656 includes two openings 655, 657, each configured to accommodate one of the signal detector heads 200. A plurality of fiber-positioning holes 658 is provided around each of the openings 655, 657. FIGS. 5 and 6 show only a portion of each of the transmission fibers 180 extending from the interface plate 660. In the illustrated embodiment, the transmission fibers 180 are connected to the interface plate 660 in a rectangular configuration, and the fiber-positioning holes 658 formed in the base 656 are in a circular configuration so as to reformat the transmission fibers 180 from the rectangular configuration at the first ends thereof to a circular configuration at the second ends thereof.

Figure 7:
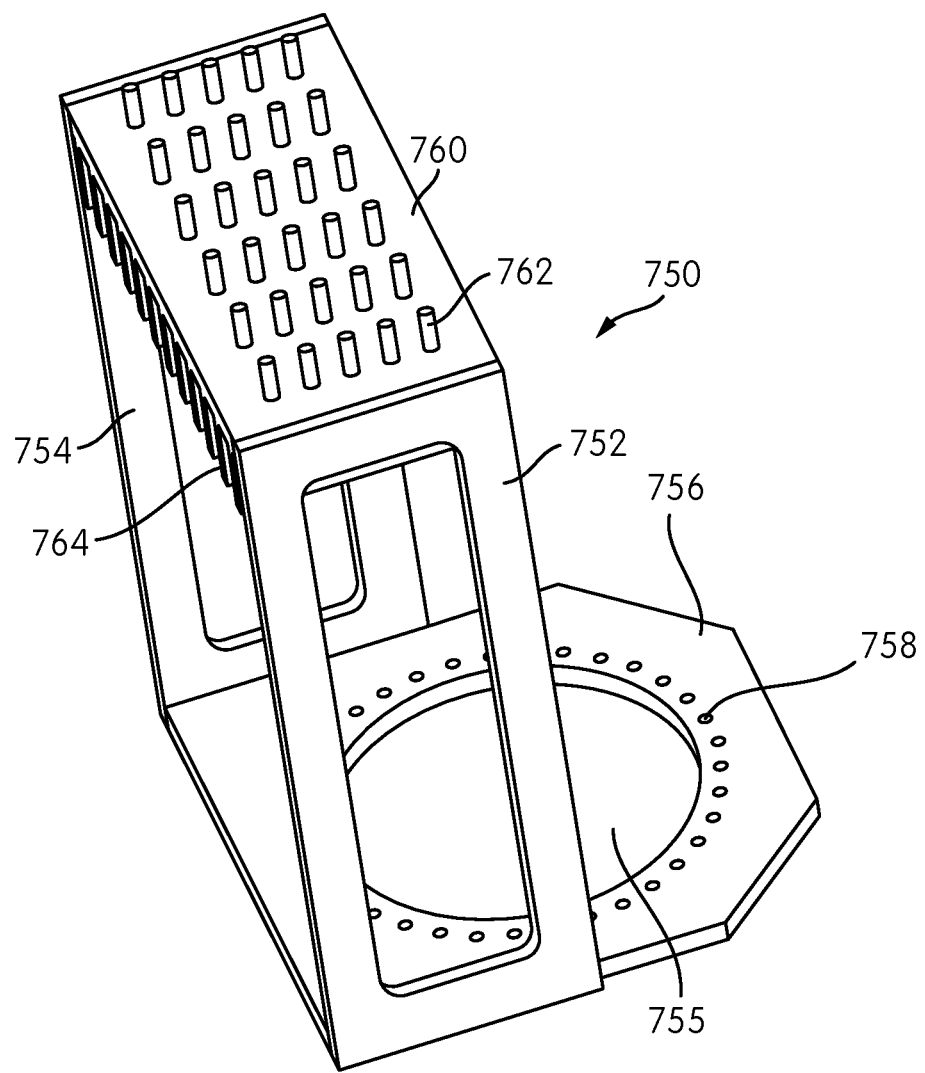
FIG. 7 is a top perspective view of an alternate embodiment of a fiber reformatter.

FIG. 7 is a perspective view of an alternative embodiment of a reformatter frame 750. Reformatter frame 750 includes sides 752, 754 and a base 756 having an opening 755 formed therein with a plurality of fiber-positioning holes 758 positioned around the opening 755 in a generally circular configuration. An interface plate 760 is attached to the sides 752, 754 of the frame 750 at an end thereof opposite the base 756. Interface plate 760 includes a plurality of coupling elements 762, e.g., ferrules, and may include heat dissipating fins 764 disposed on a side of the interface plate 760 opposite the coupling elements 762. Each coupling element 762 corresponds to a fiber-receiving opening (not shown) formed through the interface plate 760. As can be seen in FIG. 7, the coupling elements 762 are arranged in a rectangular configuration of six rows of five coupling elements 762 each. The number of openings 758 formed in the base 756 preferably corresponds to the number of coupling elements 762 formed in the interface plate 760. Thus, it can be appreciated that the reformatter frame 750 shown in FIG. 7 has half the capacity of the reformatter frame 150 shown in FIG. 1, and that the reformatter frame 150 corresponds essentially to a doubling of the reformatter frame 750 with a second opening 755 and corresponding fiber-positioning holes 758 surrounding the opening and six additional rows of five coupling elements 762 attached to the interface plate 760. However, one of skill in the art would appreciate that reformatter frame 750 could be configured to have the same capacity, or more or less capacity to that of reformatter frame 150 shown in FIG. 1.

Figure 8:
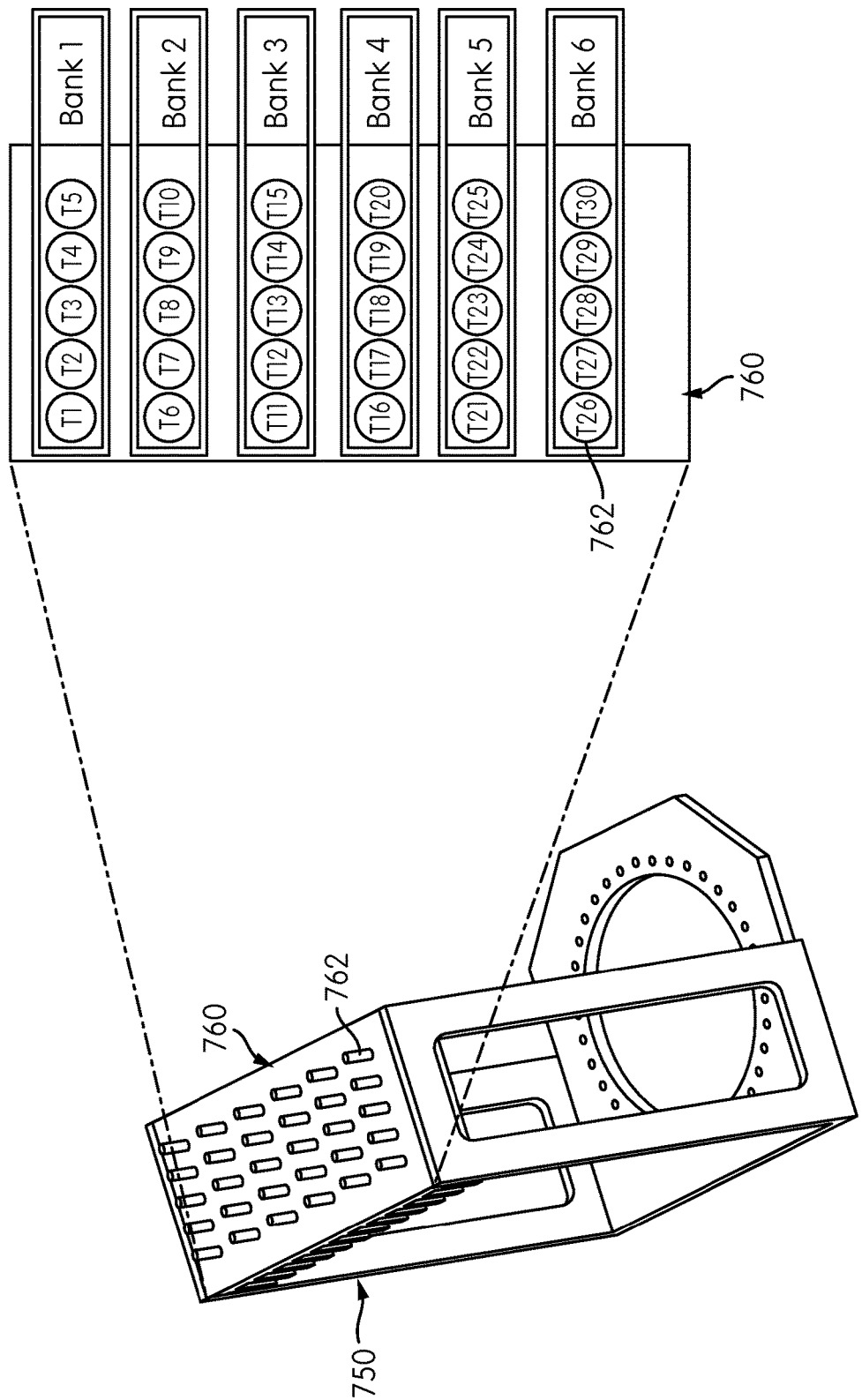
FIG. 8 shows the fiber position mapping in the interface plate of the fiber reformatter shown in FIG. 7.

FIG. 8 shows an exemplary mapping of the spatial arrangement of fiber positions in the interface plate 760 of the reformatter frame 750. As shown in FIG. 8, the interface plate 760 includes six rows, or banks, of five fiber positions each, designated T1-T5, T6-T10, T11-T15, T16-T20, T21-T25, and T26-T30.

Figure 9:
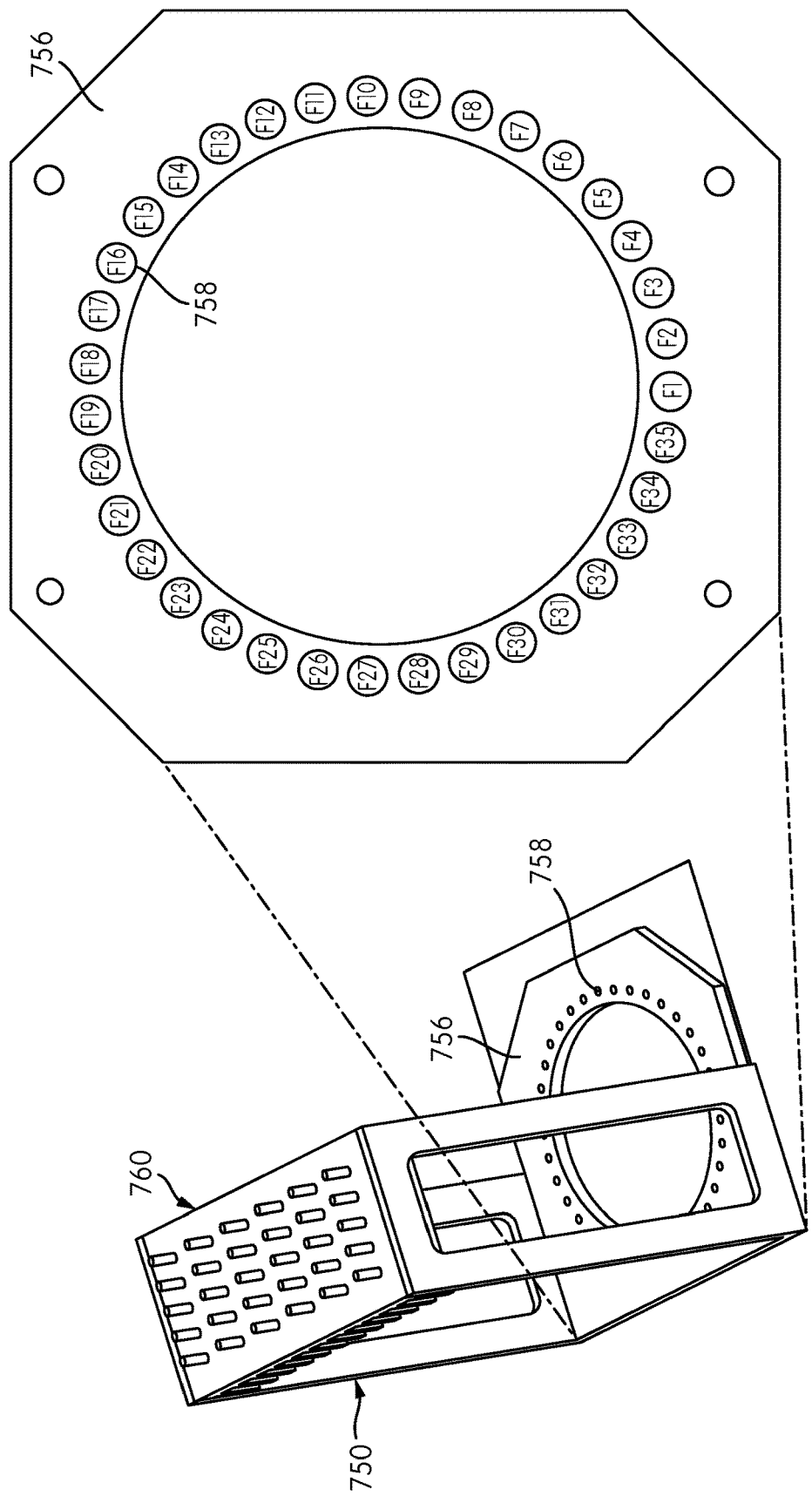
FIG. 9 shows the fiber position mapping in the baseplate of the fiber reformatter shown in FIG. 7.

FIG. 9 shows a mapping of the spatial arrangement of fiber positions of the fiber-positioning holes 758 formed in the base 756 of the reformatter frame 750. In the illustrated embodiment, 35 fiber-positioning holes 758 are formed in the base 756, and are designated F1, F2, F3, F4, . . . F35, starting at the lower (six o'clock) position with respect to the opening 755.

FIG. 10 is a table showing an exemplary mapping of the rectangularly-arranged interface positions T1-T30 in the interface plate 760 to thirty of the circularly-arranged fiber-positioning hole positions F1-F35 in the base 756. This is exemplary only; other mappings between the fiber positions in the interface plate 760 and the fiber positions in the base 756 are contemplated. In this embodiment, the number of interface positions in the interface plate 760 is exceeded by the number of fiber-positioning holes in the base 756 (e.g., 30 vs. 35). Fluorescent calibration targets can be placed in the additional fiber-positioning holes in the base to test and/or calibrate the signal detectors of the signal detector head 200.

In an alternative embodiment, the number of interface positions in the interface plate 760 is equal to the number of fiber-positioning holes in the base 756 (e.g., 30). It has been determined that the autofluorescence of the signal transmission fibers can also be used as a fluorescent calibration target. For example, autofluorescence of the signal transmission fibers can be used to determine the rotary positions of the detector carrier 250 at which signal measurements should be taken. An exemplary process is as follows.

Figure 11:
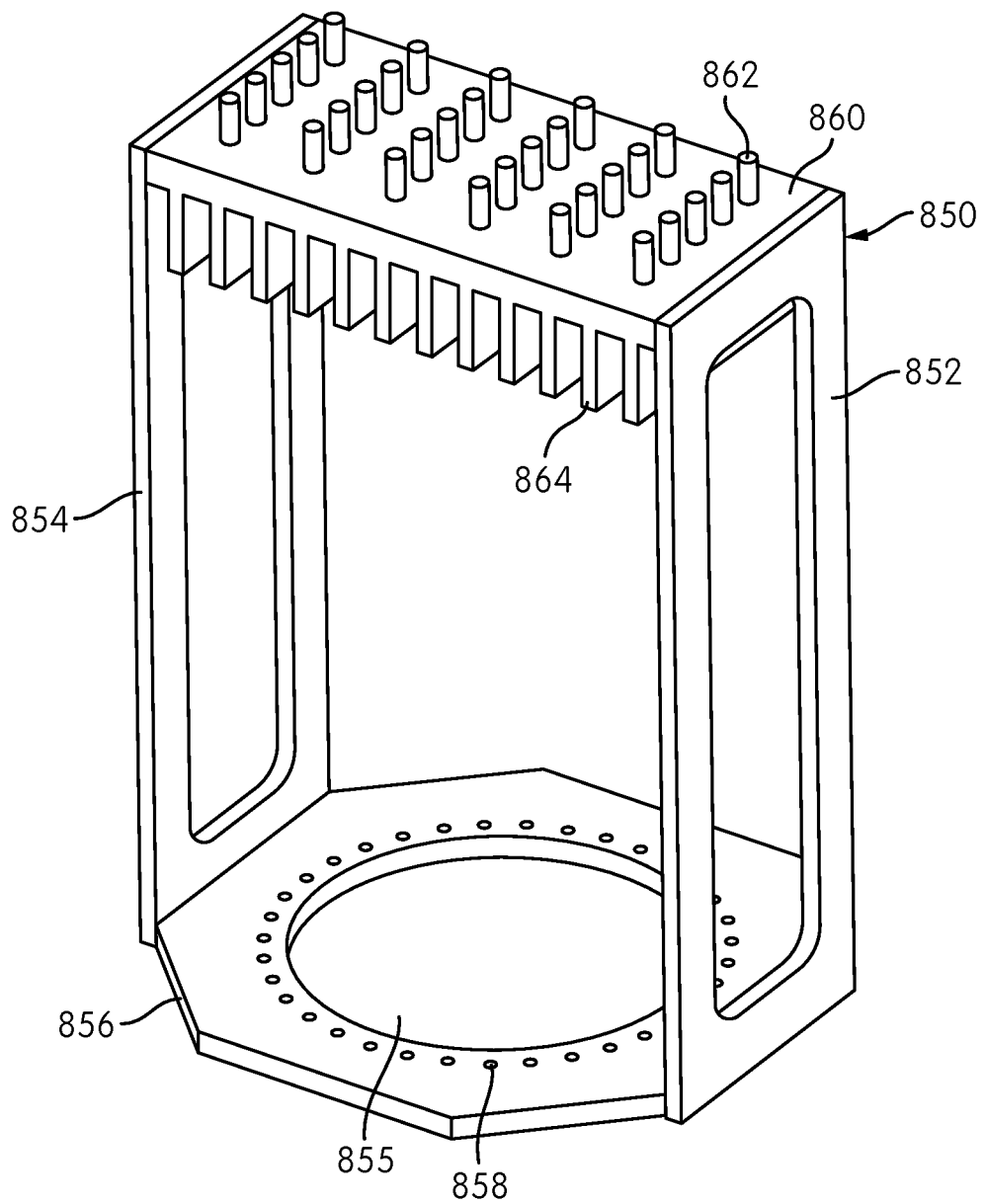
FIG. 11 is a top perspective of an alternate embodiment of a fiber reformatter.

Starting at a known rotary position, e.g., as determined by a home flag associated with the detector carrier 250, the detector carrier 250 can be rotated, counting steps of the motor 352, until the autofluorescence signal detected by each signal detector 300—each of which may be configured to detect a signal of a different wavelength—reaches a peak. Due to manufacturing and assembly tolerances, the number of motor steps at which each signal detector detects a peaks signal may be somewhat different. For example, in a system including five signal detectors 300, one signal detector 300 may peak at 130 steps from the home flag position, another at 131 steps, another at 132 steps, another at 129 steps, and another at 130 steps. The calibrated position at which a measurement is taken may be determined as to be the closest whole number of steps to the average of the five measurements, i.e., 130 steps (from an average of 130.4 steps) from the home position. If the tolerances in the placement of the fiber positioning holes 758 are sufficiently small, so that the number of motor steps between fibers is known and repeatable, no further calibration is necessary. Subsequent measurements can be taken every known number of steps after the calibrated position of the first measurement. If the tolerances are not sufficiently small, measurement positions for all fibers can be calibrated in a similar manner—i.e., by stepping off the motor for each fiber position and taking an average of the number of steps at which the signal detectors detect peak signals. It may be desirable to perform this calibration procedure at final assembly of the apparatus, at laboratory installation of the apparatus, after any service is performed on the apparatus, or before each time the apparatus is operated. FIG. 11 shows an alternative embodiment of a thirty-fiber reformatter frame 850, including sides 852, 854, a base 856 with an opening 855 and fiber-positioning openings 858 surrounding opening 855, and an interface plate 860 having coupling elements 862 and heat dissipating fins 864 connected to an end of the frame 852 opposite the base 856. Fiber reformatter frame 850 is comparable to the frame 750 shown in FIG. 7 and accommodates thirty transmission fibers (not shown in FIG. 11) configured at the first ends thereof at the interface plate 860 in a rectangular configuration of six rows of five fibers each and configured at the second ends thereof at the base 856 in a circular configuration disposed within the fiber-positioning holes 858 surrounding the opening 855. The reformatter frame 850 shown in FIG. 11 differs from the reformatter frame 750 shown in FIG. 7 in that the base 856, the opening 855, and fiber-positioning openings 858 are substantially centered with respect to the interface plate 860. In the reformatter frame 750 shown in FIG. 7, on the other hand, the base 756, openings 755, and fiber-positioning openings 758 are laterally offset with respect to the center of the interface plate 760.

Signal Detector Head

Figure 12:
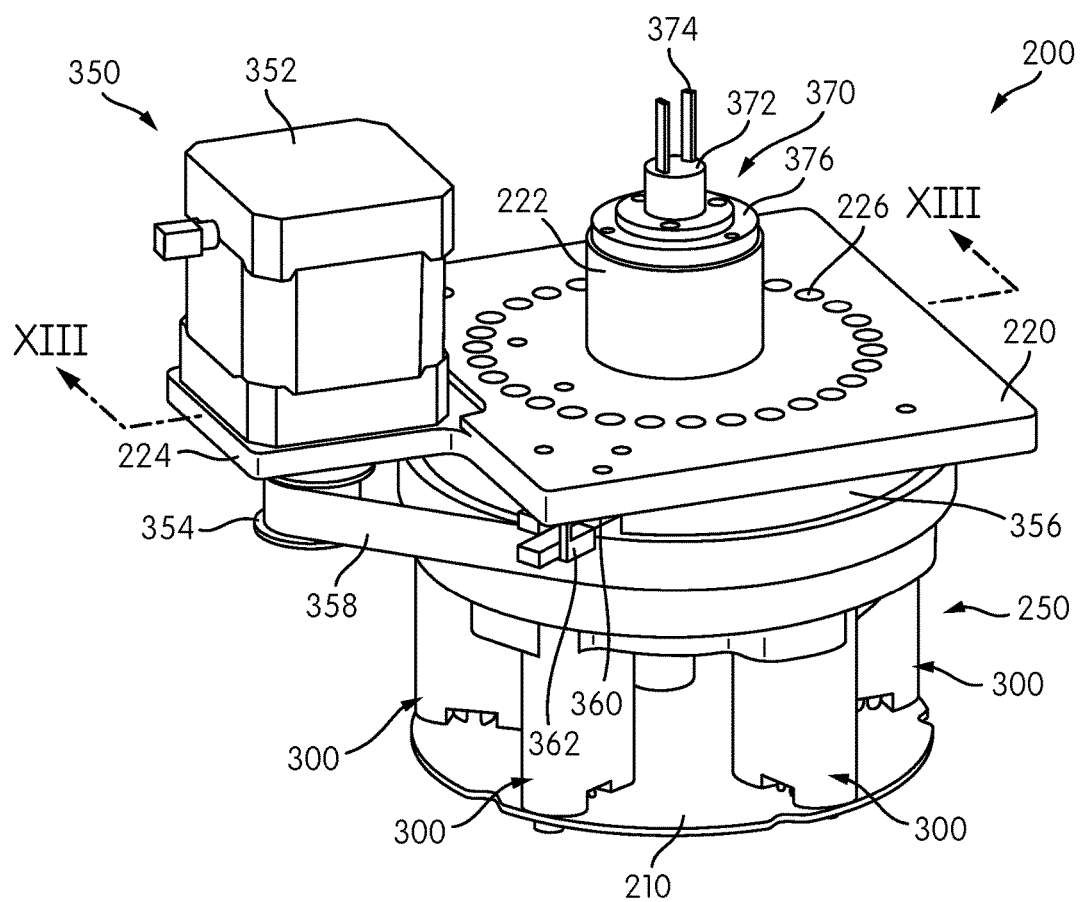
FIG. 12 is a perspective view of a signal detector head.

The signal detector head 200 is shown in FIG. 12. The signal detector head 200 may be attached to a reformatter frame (150, 650, 750, 850) and is constructed and arranged to index one or more signal detectors into operative positions with respect to each transmission fiber disposed in a fiber-positioning hole of the base of the reformatter frame. Although, signal detector head 200 is configured to be coupled to any reformatter frame, including reformatter frames 150, 650, 750 and 850 described herein, for simplicity of the description, the signal detector head 200 will be described in the context of its implementation on reformatter frame 150 shown in FIG. 1.

In the embodiment shown in FIG. 12, the signal detector head 200 includes a base plate 220 configured to be attached to the base 156 of the reformatter frame 150 and including a plurality of fiber tunnels 226 arranged in a configuration corresponding to the spatial arrangement of fiber-positioning holes 158 formed in the base 156 of the reformatter frame 150 so that each fiber tunnel 226 will align with a corresponding one of the fiber-positioning holes 158.

In general, the signal detector head is configured to move one or more signal detectors to sequentially place each signal detector into an operative position with respect to each transmission fiber 180 to detect a signal transmitted by the transmission fiber. The signal detector head 200 further includes a detector carrier 250, which, in the illustrated embodiment, comprises a carousel that carries a plurality of signal detectors 300 in a circular pattern. In the illustrated embodiment, the signal detector head 200 includes six individual signal detectors 300, each mounted on a printed circuit board 210 and each configured to excite and detect a different emission signal or an emission signal having different characteristics.

As will be described in further detail below, the detector carrier 250 is configured so as to be rotatable with respect to the base plate 220. A detector drive system 350 constructed and arranged to effect powered movement, e.g., rotation, of the detector carrier 250 includes a drive motor 350 supported on a motor mount portion 224 of the base plate 220. A drive belt 358 is disposed on an output shaft wheel 354 of the motor 352 and around a pulley wheel 356 that is attached to or part of the detector carrier 250. As can be appreciated, rotation of the output shaft wheel 354 of the motor 352 causes a corresponding rotation of the pulley wheel 356 and the detector carrier 250 via the belt 358.

As would be further appreciated by persons of ordinary skill in the art, the configuration of the detector drive system 350 is exemplary, and other mechanisms and arrangements may be employed to effect powered movement of the detector carrier 250. For example, the output shaft wheel 354 may comprise an output gear that directly engages gear teeth formed about the outer periphery of the pulley wheel 356, or the pulley wheel 356 could be coupled to the output shaft wheel 354 indirectly by a gear train comprising one or more intermediate gears between the output shaft wheel (gear) 354 and the pulley wheel 356. Alternatively, a drive motor could be configured with its rotating output shaft attached concentrically to the detector carrier 250 and its axis of rotation so that rotation of the output shaft by the motor causes a direct corresponding rotation of the detector carrier 250. Other arrangements and configurations for effecting powered movement of the detector carrier 250 will be appreciated by persons of ordinary skill in the art. In particularly preferred embodiments, the detector carrier 250 and detector drive system 350 are configured to provide for rotation of the detector carrier 250 in a single direction.

Motor 352 is preferably a stepper motor and may include a rotary encoder. The detector carrier 250 may include one or more positional or status feedback sensors. For example, the detector carrier 250 may include a home flag 360 that is detected by an optical detector 362 for indicating a rotational "home" position of the carrier 250. Optical sensor 360 may comprise a slotted optical sensor comprising an optical transmitter and receiver in which the path between the transmitter and receiver is broken by the passage of the home flag 360. Persons of ordinary skill in the art will recognize, however, that other sensors for indicating a home position may be used. Such sensors may comprise proximity sensors, magnetic sensors, capacitive sensors, etc.

A rotary connector transmits data and/or power signals between the rotating detector carrier 250 and the signal detectors 300 carried thereon, and a non-rotating reference environment, such as a controller and power source as described in more detail below. In the illustrated embodiment, the base 220 of the signal detector head 200 includes cylindrical housing 222 projecting upwardly from a planar portion of the base 220, and a slip ring connector 370 is positioned at an end of the cylindrical housing 222. The slip ring connector 370 includes a rotating element disposed inside the cylindrical housing 222 and a non-rotating element 372, attached or otherwise coupled to the non-rotating cylindrical housing 222 by an intermediate ring 376, to which are attached data/power cables 374. The slip ring connector 370 transmits data and/or power signals between the rotating detector carrier 250 and the signal detectors 300 carried thereon, and a non-rotating reference environment, such as a controller and power source as described in more detail below.

Figure 13:
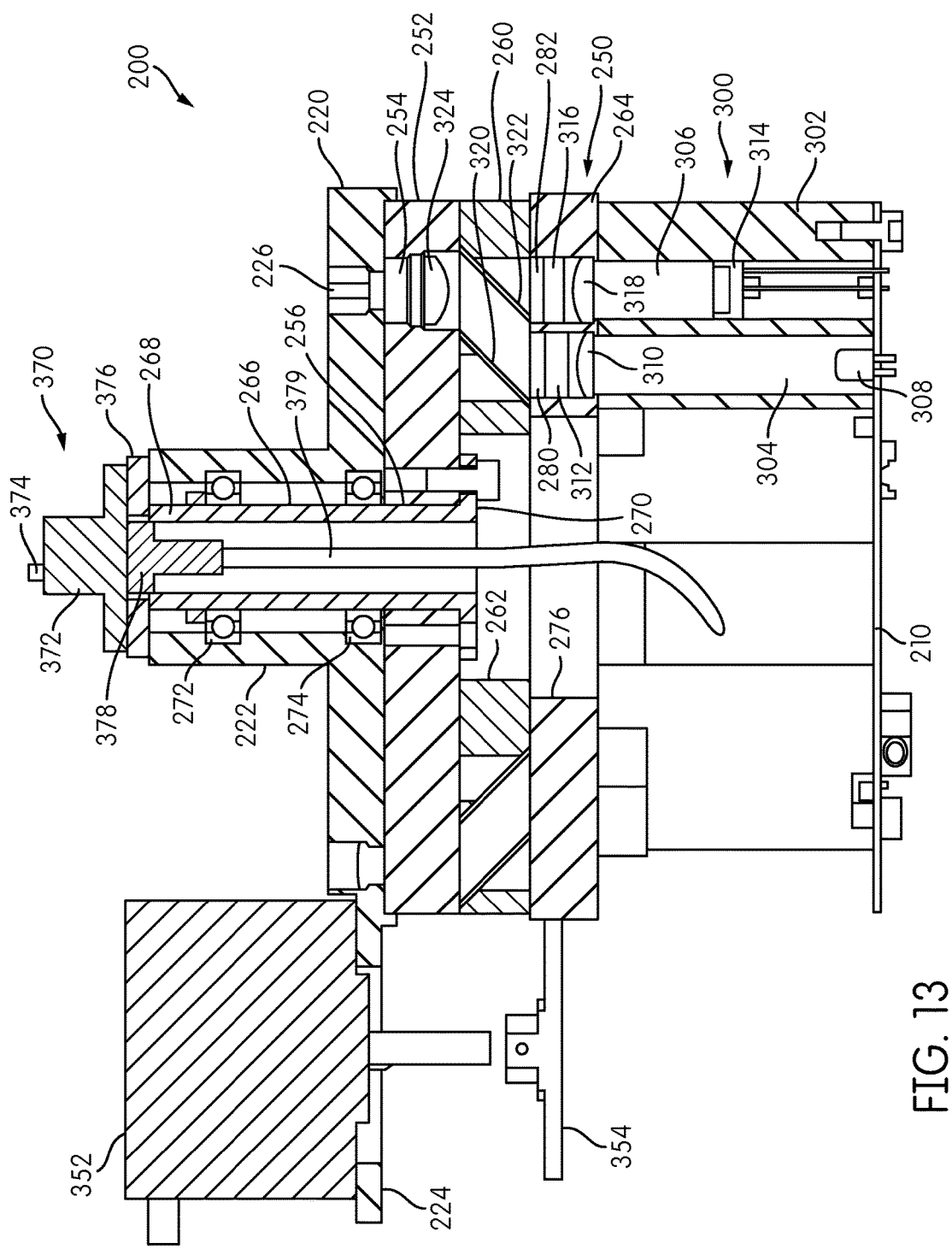
FIG. 13 is a transverse cross-section of the signal detector head along the line XIII-XIII in FIG. 12.

Further details of the signal detector head 200 are shown in FIG. 13, which is a transverse cross-sectional view of the detector head 200 along the line XIII-XIII in FIG. 12. Each signal detector 300 includes a detector housing 302 within which are formed an excitation channel 304 and an emission channel 306, which, in the illustrated embodiment, are generally parallel to one another. An excitation source 308, such as an LED, is mounted on the printed circuit board 210 at the base of the excitation channel 304. An emission detector 314, such as a photodiode, is coupled to the printed circuit board 210 and is disposed within the emission channel 306.

The detector carrier 350 further includes, positioned adjacent the signal detector housing 302, a filter plate 264 having a central opening 276 formed therein and defining an annulus. Within the annulus, an emission filter opening 282 and an excitation filter opening 280 are formed in alignment with the emission channel 306 and the excitation channel 304, respectively, of each signal detector housing 302. An excitation lens 310 and an excitation filter 312 are disposed in the excitation opening 280. Although a single excitation lens 310 and a single excitation filter 312 are shown in FIG. 13, the signal detector 300 may include multiple excitation filters and/or multiple excitation lenses. Similarly, an emission filter 316 and an emission lens 318 are disposed in the emission opening 282. Although a single emission filter 316 and a single emission lens 318 are shown in FIG. 13, the signal detector 300 may include multiple emission lenses and/or multiple emission filters.

The detector carrier 250 further includes, adjacent the filter plate 264, a mirror plate 260 having a central opening 262 and defining an annulus. The annulus of the mirror plate 260 has formed therein openings aligned with the emission opening 282 and the excitation opening 280 formed in the filter plate 264 for each signal detector 300. A mirror 320 is disposed in the mirror plate 260 in general alignment with the excitation channel 304, and a dichroic filter 322 is disposed in the mirror plate 260 in general alignment with the emission channel 306. Mirror 320 is oriented at an angle (e.g. 45°) with respect to the excitation channel 304 so as to be configured to redirect a light beam.

The detector carrier 250 further includes an objective lens plate 252 having a central opening 256 formed therein and defining an annulus. A lens opening 254 is formed through the annulus of the objective lens plate 252 in general alignment with the emission channel 306 of each signal detector 300. An objective lens 324 is disposed within the lens opening 254.

The base plate 220 is disposed adjacent the objective lens plate 252 and includes fiber tunnels 226 formed about the perimeter thereof. Although base plate 220 and objective lens plate 252 are depicted as abutting one-another in FIG. 13, it is contemplated that there can be a designated distance, forming an air gap, between the base plate 220 and the objective lens plate 252. Also, objective lens plate 252 and mirror plate 260 are depicted as abutting one-another in FIG. 13, it is contemplated that there can be a designated distance, forming an air gap, between the objective lens plate 252 and the mirror plate 260.

The detector carrier 250, comprising the objective lens plate 252, the mirror plate 260, and the filter plate 264, as well as the signal detectors 300 carried thereon, are rotatable with respect to the base plate 220 so that each objective lens 324 associated with each of the signal detectors 300 can be selectively placed into operative alignment with one of the fiber tunnels 226 disposed in the base plate 220. Thus, in the illustrated embodiment having six signal detectors 300, at any given time, six of the fiber tunnels 226 are in operative, optical alignment with one of the objective lenses 324 and its corresponding signal detector 300.

Figure 14:
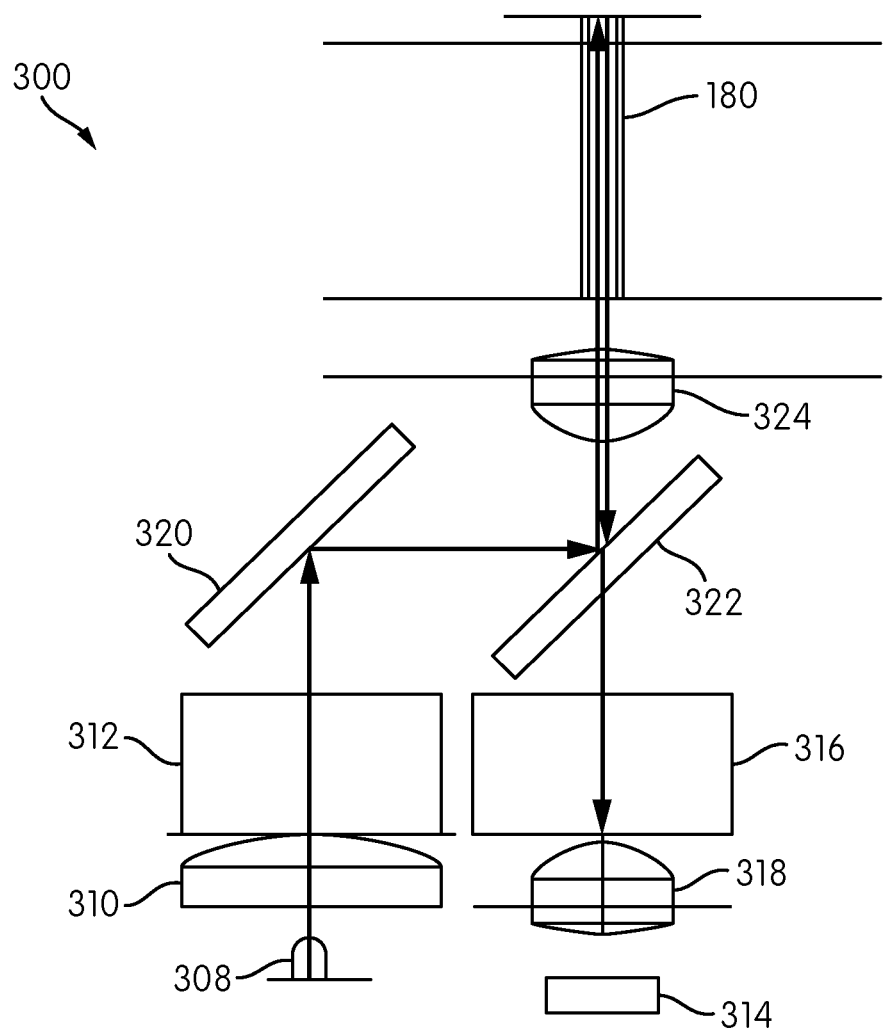
FIG. 14 is a schematic view of an embodiment of an exemplary optical path within a signal detector.

Operation of the signal detector 300 in an exemplary embodiment is illustrated schematically in FIG. 14. The detector 300 shown is a fluorometer that is constructed and arranged to generate an excitation signal of a particular, predetermined wavelength that is directed at the contents of a receptacle to determine if a probe or marker having a corresponding emission signal of a known wavelength is present. When the signal detector head 200 includes multiple fluorometers—e.g., six—each fluorometer is configured to excite and detect an emission signal having a different wavelength to detect a different label associated with a different probe hybridized to a different target analyte. When a more frequent interrogation of a sample is desired for a particular emission signal, it may be desirable to incorporate two or more fluorometers configured to excite and detect a single emission signal on the signal detector head 200.

Figure 15:
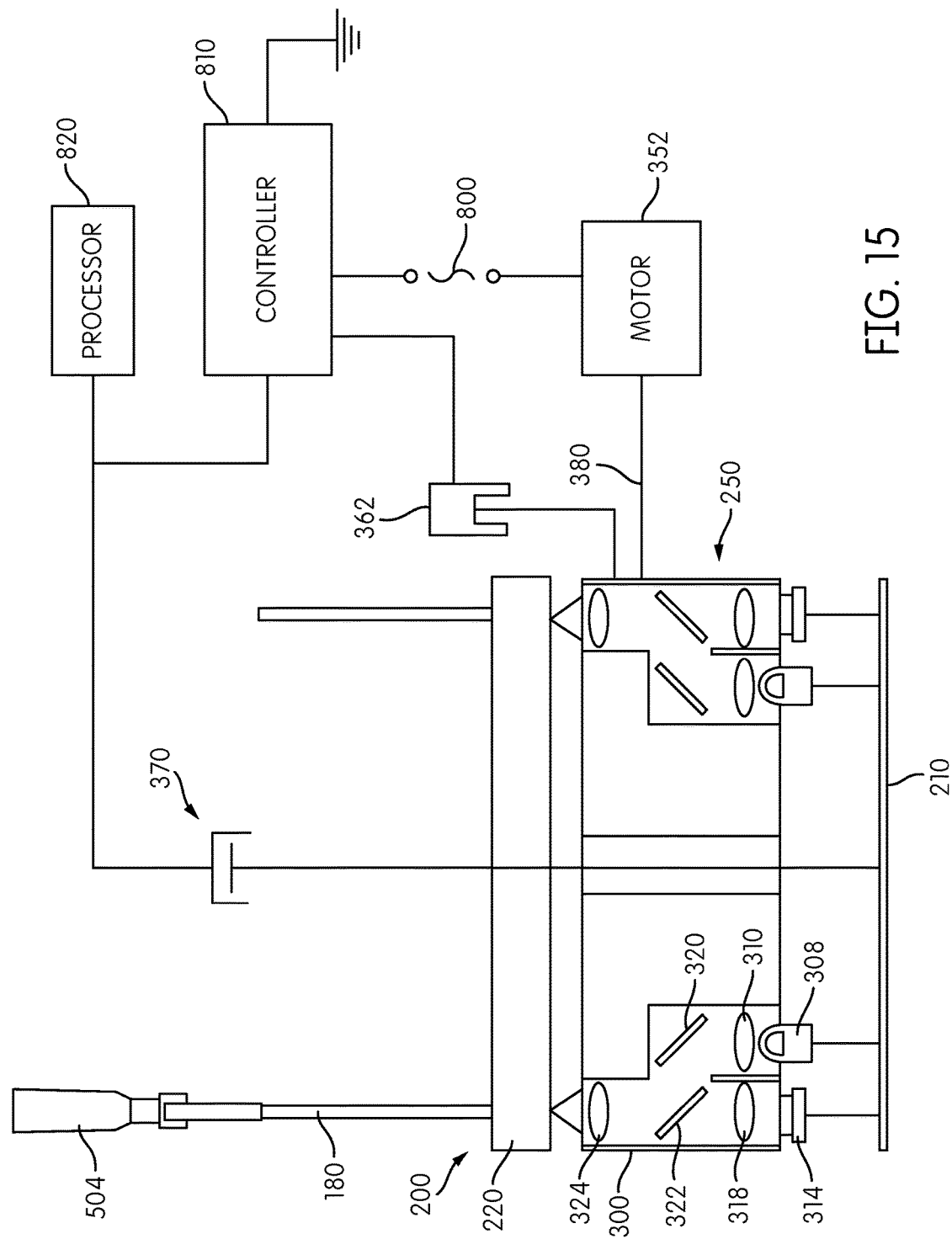
FIG. 15 is a schematic view of the signal detection module embodying aspects of the present disclosure and a power and data control system incorporated therewith.

An excitation signal is emitted by the excitation source 308. Excitation source, as noted above, may be an LED and may generate light at a predetermined wavelength, e.g. red, green, or blue light. Light from the source 308 passes through and is focused by an excitation lens 310 and then passes through the excitation filter 312. As noted, FIG. 15 is a schematic representation of the signal detector 300, and the focusing functionality provided by the excitation lens 310 may be effected by one or more separate lenses disposed before and/or after the filter element 312. Similarly, the filter functionality provided by the filter element 312 may be effected by one or more individual filters disposed before and/or after the one or more lenses that provide the focusing functionality. Filter element 312 may comprise a low band pass filter and a high band pass filter so as to transmit a narrow wavelength band of light therethrough. Light passing through the excitation lens 310 and excitation filter element 312 is reflected laterally by the mirror 320 toward the dichroic 322. The dichroic 322 is constructed and arranged to reflect substantially all of the light that is within the desired excitation wavelength range toward the objective lens 324. From the objective lens 324, light passes into a transmission fiber 180 and toward the receptacle at the opposite end thereof. The excitation signal is transmitted by the transmission fiber 180 to a receptacle so as to expose the contents of the receptacle to the excitation signal.

A label that is present in the receptacle and is responsive to the excitation signal will emit an emission signal. At least a portion of any emission from the contents of the receptacle enters the transmission fiber 180 and passes back through the objective lens 324, from which the emission light is focused toward the dichroic 322. Dichroic 322 is configured to transmit light of a particular target emission wavelength range toward the emission filter 316 and the emission lens 318. Again, the filtering functionality provided by the emission filter 316 may be effected by one or more filter elements and may comprise a high band pass and low band pass filter that together transmit a specified range of emission wavelength that encompasses a target emission wavelength. The emission light is focused by the emission lens 318, which may comprise one or more lenses disposed before and/or after the filter elements represented in FIG. 14 by emission filter 316. The emission lens 318 thereafter focuses the emission light of the target wavelength at the detector 314. In one embodiment, the detector 314, which may comprise a photodiode, will generate a voltage signal corresponding to the intensity of the emission light at the prescribed target wavelength that impinges the detector.

Returning again to FIG. 13, a flanged tube 266 extends through the central opening 256 of the objective lens plate 252 and through the cylindrical housing 222 of the base plate 220. The flanged tube 266 includes a cylindrical tube 268 extending through the central opening 256 and the cylindrical housing 222 and a radial flange 270 disposed within the central opening 262 of the mirror plate 260 and secured by suitable fasteners, such as screws or bolts, to the objective lens plate 252. Longitudinally-spaced bearing races 272, 274 are disposed between the interior of the cylindrical housing 222 and the exterior of the cylindrical tube 268 of the flanged tube 266. Thus, as can be appreciated, the flanged tube 266 will rotate, with the detector carrier 250, with respect to the base plate 220 and the cylindrical housing 222.

Further details of an exemplary representation of the slip ring 370 are also shown in FIG. 13. The slip ring connector 370 is disposed at the end of the cylindrical tube 268 opposite the radial flange 270. As noted above, the cylindrical tube 268 rotates with the detector carrier 250, while the cylindrical housing 222 remains stationary with the base plate 220. The slip ring connector 370, which may comprise slip rings and brushes as are known, includes stationary components attached or otherwise coupled to the cylindrical housing 222 and rotating components attached or otherwise coupled to the rotating cylindrical tube 268. In general, components 372, 376 represent non-rotating portion(s) of the slip ring 370 in which fixed contact components, such as the brush(es), are located, component 378 located inside tube 268 represents rotating portion(s) of the slip ring 370 that rotate with the tube 268 and in which rotating contact elements, such as the ring(s) are located, and cable 379 represents a power and/or data conductor(s) connecting component 378 with the printed circuit board 210 and which rotates with the printed circuit board 210 and the signal detector carrier 250.

As the detector carrier 250 rotates, each of the signal detectors 300 is sequentially placed in an operative position with respect to a second end of a different transmission fiber 180 to interrogate (i.e., measure a signal from) an emission signal source located at a first end of the transmission fiber 180. The detector carrier 750 pauses momentarily at each transmission fiber 180 to permit the signal detector 300 to detect an emission signal transmitted through the transmission fiber 180. Where the signal detector 300 is a fluorometer, the detector carrier pauses momentarily to permit the signal detector to generate an excitation signal of a specified wavelength that is transmitted by the transmission fiber 180 to the emission signal source (receptacle) and to detect fluorescence of a specified wavelength excited by the excitation signal that is emitted by the contents of the receptacle and transmitted by the transmission fiber 180 to the fluorometer. Thus, in an embodiment, each transmission fiber 180 can be employed to transmit both an excitation signal and the corresponding emission signal, ad each signal detector can be used to scan multiple transmission fibers and associated emission signal sources.

The emission signal source associated with each transmission fiber 180 is interrogated once by each signal detector 300 for every revolution of the detector carrier 250.

Where the signal detector head 200 includes multiple signal detectors 250 configured to detect different signals, each emission signal source is interrogated once for each different signal for every revolution of the detector carrier. Thus, in the case of a nucleic acid diagnostic assay, which may include PCR amplification, the contents of each receptacle is interrogated for each target analyte corresponding to the different probes employed (as indicated by different colored labels) once for each revolution of the detector carrier 250.

In one embodiment, in which base plate 220 of the signal detector head 200 includes thirty (30) fiber tunnels for thirty (30) transmission fibers 180, the signal detector carrier rotates one revolution every four (4) seconds, stopping at least ten (10) milliseconds at each fiber tunnel to measure an emission signal transmitted by the associated transmission fiber. Again, if the signal detector head include multiple signal detectors (e.g., six (6) fluorometers), the signal detector head will measure an emission for each of the six different wavelengths of interest once every four (4) seconds. Accordingly, time vs. emission signal intensity data can be generated for each receptacle for each wavelength.

When performing PCR, it is not necessary to synchronize the signal data acquisition with the thermal cycles of the PCR process. That is, it is not necessary that the emission signal of each receptacle be measured at the same temperature point (e.g., 95° C.) in the PCR cycle. By recording data every four seconds during the entire PCR process, a sufficient number of data points will be collected at each temperature of the PCR thermal cycle. The signal emission data is synchronized with specific temperatures by recording a time stamp for each emission signal measurement and a time stamp for each temperature of the thermal cycling range. Thus, for example, to identify all signal measurements occurring at a temperature of 95° C., the time stamps of the signal measurements are compared to the temperature time stamps corresponding to a temperature of 95° C.

The time duration of a thermal cycle is variable, depending on the assay being performed. The minimum time interval is dictated by how fast the thermocycler can ramp temperatures up and down. For a cycler that can ramp the vial filled with fluid from 55° C. to 95° C. in about 15 seconds, an exemplary cycle would be anneal at 55° C. for 25 seconds, a 15 second from 55° C. to 95° C., denature at 95° C. for 5 seconds, and 15 second ramp back down from 95° C. to 55°, and then begin another cycle with a 25 second anneal, Thus, this exemplary anneal-denature cycle would be a 60 second cycle.

The control and data acquisition system of the signal detector head 200 is shown schematically in FIG. 15. As shown in FIG. 15, the detector carrier 250 carries one or more signal detectors 300, each of which may, in one embodiment, include an excitation source 308, an excitation lens 310, a mirror 320, a dichroic 322, an objective lens 324, an emission lens 318, and an emission detector 314 as described above. Each receptacle 504 carried in, e.g., a processing module 500 (see FIGS. 2-4), is coupled to a transmission fiber 180 that terminates in the base plate 220 of the signal detector head 200. Motor 352 is mechanically coupled to the detector carrier 250 by a motor coupler 380 to effect powered movement (e.g., rotation) of the detector carrier 250. A controller 810 may be coupled to a controllable power source 800 and to the motor 352 for providing motor control signals and receiving motor position feedback signals, e.g., from a rotary encoder. Controller 810 may also be coupled to other feedback sensors, such as the home sensor 360, for detecting a rotational position of the detector carrier 250. Controller 810 also provides controlled power signals, via the slip ring connector 370, to the excitation sources 308 rotatably carried on the detector carrier 250 and coupled to the printed circuit board 210. The functionality of controller 810 may be provided by one controller or multiple controllers in functional communication with each other. Moreover, one or more controllers, or one or more component(s) thereof, may be carried on the rotating portion of the detector head 200, such as on the printed circuit board 210. Voltage signals from the emission detectors 314, coupled to the printed circuit board 210, and other data may be carried from the detector carrier 250, via the slip ring connector 370, to a processor 820 for storing and/or analyzing the data. Alternatively, processor 820, or one or more component(s) thereof, may be carried on the rotating portion of the detector head 200, such as on the printed circuit board 210.

Figure 16:
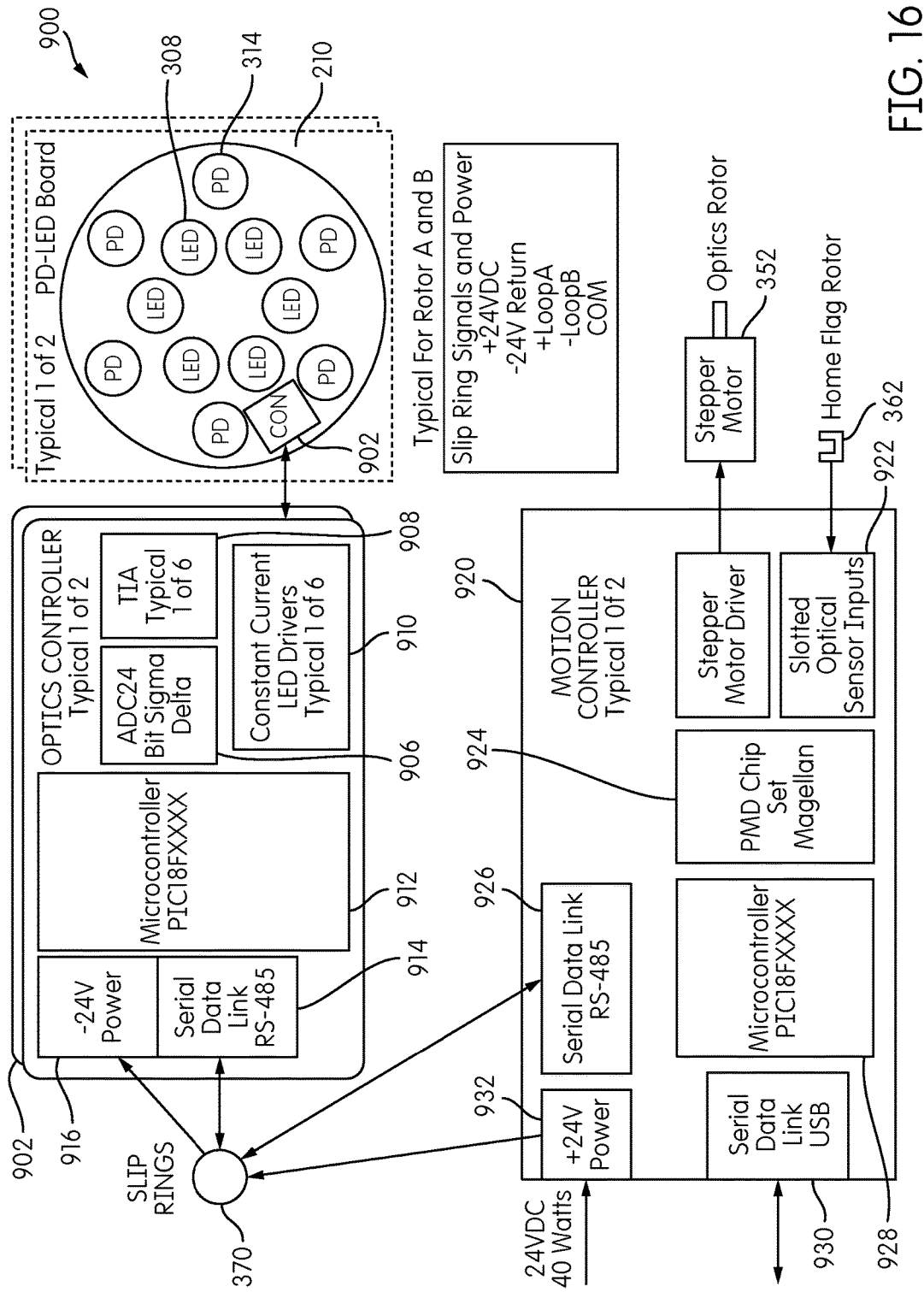
FIG. 16 is a schematic view of a control system for the signal detector head.
Figure 17:
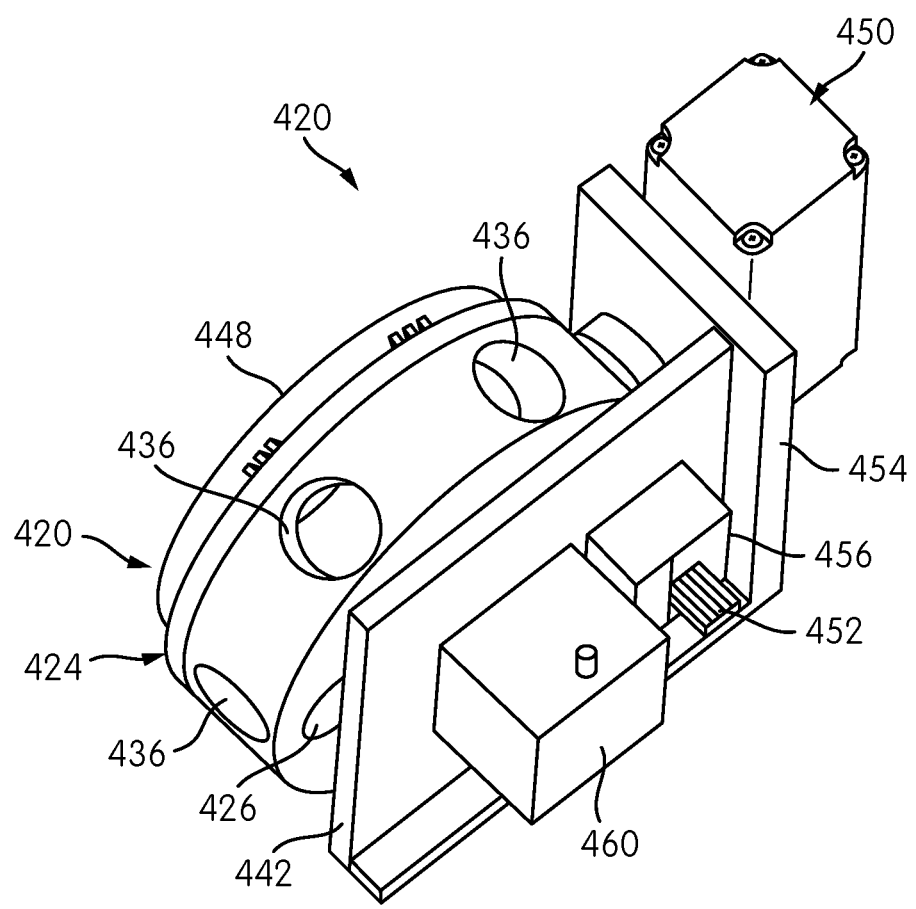
FIG. 17 is a perspective view of an alternate embodiment of a signal detector head.
Figure 18:
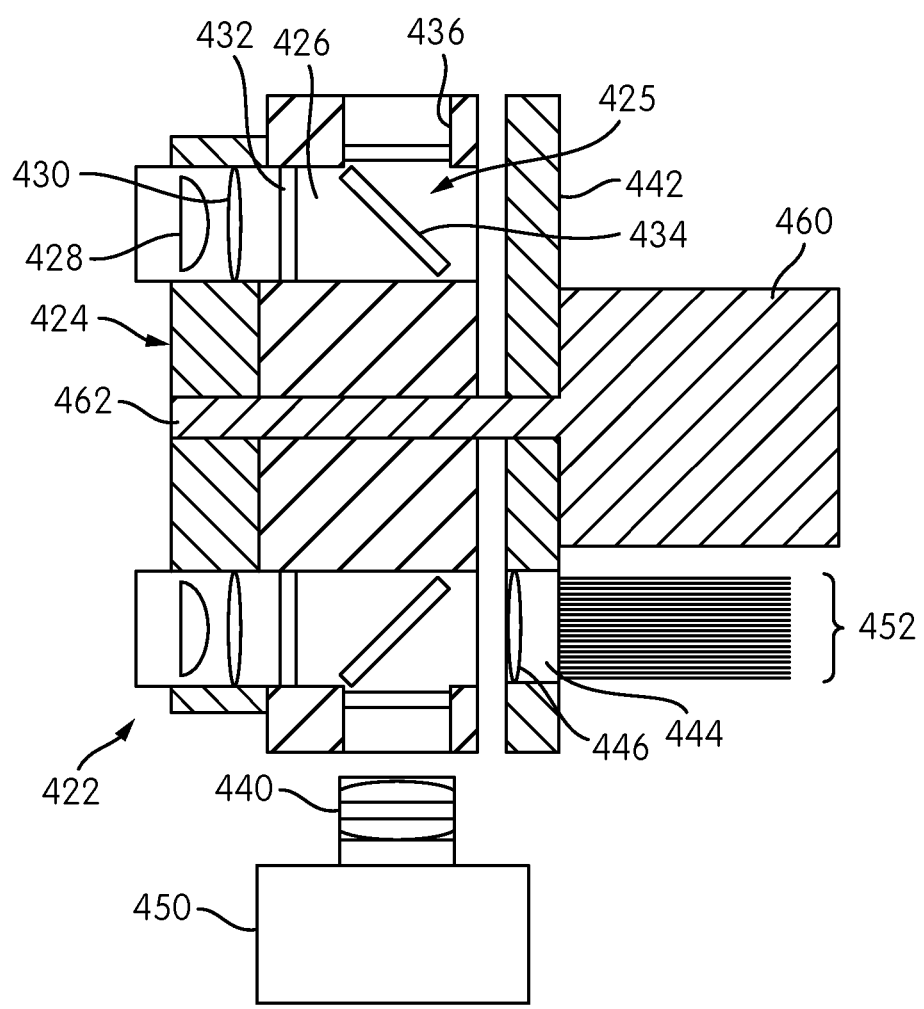
FIG. 18 is cross sectional view of the signal detector head of FIG. 17.

An exemplary control configuration of the signal detector head 200 is represented by reference number 900 in FIG. 16. An optics controller 902 may be provided for each detector carrier, or rotor, and coupled to the printed circuit board 210 to which the excitation sources (LED) 308 and emission detectors (PD (photodiode)) 314 are attached. Each optics controller 902 may include a microcontroller 912, e.g., a PIC18F-series microcontroller available from Microchip Technology Inc., an analog to digital converter 906, and an integrated amplifier 908 (e.g., one for each emission detector (PD) 314). A constant current driver 910 (e.g. one for each excitation source 308) is controlled by the microcontroller 928 and generates control signals (e.g., controlled power) to the excitation source 308. Controller 902 receives power at 916 (e.g., 24 V) from the slip ring connector 370 and includes a serial data link RS-485 914 for commutations between the controller 902 and the slip ring connector 370.

An exemplary control configuration 900 may include a motion controller 920 for each detector drive 350 (see FIG. 12). At 932, motion controller 920 receives power, e.g., 24 VDC, 40 watts from controllable power source 800 (see FIG. 15), that is transmitted to the optics controller 902 via the slip ring 370. Motion controller 920 may communicate with an external controller via a serial data link 930. In one embodiment, controller 920 communicates with a controller of the thermocycler to synchronize operation of the signal detector head 200 with operation of the thermocycler. Controller 920 may include a serial data link RS-485 926 for communications between the controller 920 and the slip ring 370. Controller 920 may further include a microcontroller 928, e.g., a PIC18F-series microcontroller available from Microchip Technology Inc. and a PMD chip set 924, which is a motor controller to control the stepper motor. A stepper motor driver 936 is controlled by the microcontroller 928 and generates motor control signals for the motor 352 of the optics rotor (i.e., detector drive). A slotted optical sensor input 922 receives signals from the home flag sensor 362 and communicates such signals to the microcontroller 928.

An alternative embodiment of a signal detector head embodying aspects of the present disclosure is indicated by reference number 420 in FIGS. 22 and 23. Signal detector head 420 includes a filter wheel 422 and a camera 450 oriented in a radial focal direction with respect to the filter wheel 422. In general, signal detector head 420 employs the camera 450 to image a plurality of bundled fibers to detect a signal transmitted by each fiber. The filter wheel 422 can be indexed to selectively couple each of one or more excitation sources and emission filters with the fiber bundle and the camera 450 to direct an excitation signal of a specified characteristic, e.g., wavelength, to the fibers of the fiber bundle and to direct emission signals of a specified characteristic, e.g., wavelength, from the fibers of the fiber bundle to the camera 450.

More particularly, signal detector head 420 includes a filter wheel 422 that comprises a body 424. Body 424 may be a body or assembly of revolution configured to be rotatable about a central axis. A motor 460 is coupled to the filter wheel 422 by a transmission element 462 to effect powered rotation of the filter wheel 422. Transmission element 462 may comprise any suitable transmission means for transmitting the rotation of the motor 460 to the filter wheel 422. Exemplary transmissions include interengaged gears, belts and pulleys, and an output shaft of the motor 460 directly attached to the body 424, etc. Motor 460 may be a stepper motor to provide precise motion control and may further include a rotary encoder. The filter wheel 422 may further include a home flag for indicating one or more specified rotational positions of the filter wheel 422. Suitable home flags include slotted optical sensors, magnetic sensors, capacitive sensors, etc. A fiber bundle 452 includes a plurality of fibers fixed at the first ends thereof with respect to the filter wheel 422, e.g., to a fixed plate 442 located adjacent to the filter wheel 424, by a fiber mounting block 456. The second ends of the respective fibers are coupled to each of a plurality of signal sources positioned in a first specified arrangement, and may include receptacles (such as receptacles 504) positioned in a rectangular arrangement.

The filter wheel 422 includes one or more optics channels 425 and is movable so as to selectively index each optics channel 425 into an operative, optical communication with the fiber bundle 452 and the camera 450. Each optics channel 425 includes an excitation channel 426 formed in an axial direction within the body 424 of the index wheel 422 for transmitting an excitation signal to the fiber bundle 452 and an emission channel 436 extending radially from the excitation channel 426 to a radial opening on the outer periphery of the filter wheel 422.

An excitation source 428, e.g., a bright light LED, is disposed within the excitation channel 426. The excitations sources 428 of all the emission channels 436 may be connected to a printed circuit board 448. One or more lenses 430 and one or more excitation filters 432 are positioned within the excitation channel 426 to condition light emitted by the source 428. Each optics channel 425 may be configured to generate and transmit an excitation signal of a specified wavelength. In such an embodiment, filter(s) 432 are configured to transmit light at the desired wavelength.

Each channel 425 includes a dichroic 434 configured to transmit that portion of the excitation signal that is at or near the prescribed excitation wavelength.

When the optics channel 425 is in optical communication with the fiber bundle 452—such as by rotating he filter wheel 424 until the optics channel 425 is aligned with a fiber tunnel 444 within, or adjacent to, which the fiber bundle 452 is secured—an objective lens 446 transmits the excitation signal from the excitation channel 426 into each fiber of the fiber bundle 452. Emissions from the emissions sources at the opposite ends of the fibers are transmitted by each fiber of the fiber bundle 452 back through the objective lens 446 and into the optic channel 425. Dichroic 434 may be configured to reflect light of a specified emission wavelength. Thus, that portion of the emission light transmitted by the fiber bundle 452 into the optics channel 425 that is at the specified emission wavelength is reflected by the dichroic 434 into the emission channel 436.

An emission filter 438 is disposed within the emission channel 436 and is configured to transmit light having the desired emission wavelength. The emission channel 436 terminates at a radial opening formed about the outer periphery of the body 424. In an embodiment, the optics channel 425 is oriented with respect to the camera 450 such that an optic channel 425 that is in optical communication with the fiber bundle 452 is also in optical communication with the camera 450.

When the optics channel 425 is an operative position with respect to the camera 450, the radial opening of the emission channel 436 is aligned with image relay optics 440 that transmit emission light from the emission channel 436 into the camera 450. Camera 450 then images the emission signals transmitted by all fibers in the fiber bundle 452 at once. To determine the signal transmitted by each fiber—and thus the signal emitted by the signal emission source associated with the fiber—the pixels of the camera's pixel matrix are mapped to the fiber locations within the fiber bundle to identify the one or more pixels of the pixel array that correspond to each fiber. By interrogating the signal imaged at each pixel or group of pixels associated with a fiber, the signal (e.g. the color (wavelength) and/or intensity) of the mission signal transmitted by that fiber can be determined.

Suitable cameras include CMOS camera such as the IDS UI-5490HE camera or CCD camera such as the Lumenera LW 11059 or the Allied GE4900. Preferably, the camera has at least 10 megapixels and has a high frame rate.

In an embodiment, the filter wheel 422 includes multiple (e.g., 3 to 6) optics channels 425, each configured to excite and detect an emission of a different wavelength or other specific, distinguishing characteristic. Thus by rotating the filter wheel to index each optics channel 425 with respect to the fiber bundle 452 and camera 450, signals of each distinguishing characteristic can be measure from all fibers and associated signal emission sources.

It will be appreciated that the signal detector head may include one or more additional cameras positioned and be coupled to one or more additional fiber bundles to permit simultaneous imaging of the multiple fiber bundles.

Hardware and Software

Aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as keyboards, touch screens, microphones, switches, manually-operated scanners, etc. Data output components may comprise hard drives or other storage media, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the disclosures require features or combinations of features other than those expressly recited in the claims. Accordingly, the present invention is deemed to include all modifications and variations encompassed within the spirit and scope of the following appended claims.

The invention claimed is:

1. An apparatus for transmitting an optical signal emission from the contents of each of a plurality of receptacles, said apparatus comprising:
   a processing module configured to hold the plurality of receptacles;
   a plurality of signal transmission conduits, each signal transmission conduit comprising an optical fiber coupled to the processing module to transmit an optical signal emitted by the contents of an associated one of the plurality of receptacles between a first end and a second end thereof, wherein each of the plurality of signal transmission conduits transmits both an excitation and an emission signal; and
   a conduit reformatter constructed and arranged to secure the first ends of the respective signal transmission conduits in a first spatial arrangement corresponding to a spatial arrangement of the plurality of receptacles held within the processing module, such that the first end of each signal transmission conduit is positioned to receive an emission signal emitted by the contents of the associated receptacle, and to secure the second ends of the respective signal transmission conduits in a second spatial arrangement different from the first spatial arrangement.

2. The apparatus of claim 1, wherein the first spatial arrangement is rectangular and comprises two or more rows, each row including two or more of the first ends of the signal transmission conduits.

3. The apparatus of claim 1, wherein the second spatial arrangement comprises one or more circles, whereby the second ends of a plurality of signal transmission conduits are positioned about the circumference of a circle.

4. The apparatus of claim 1, wherein the second spatial arrangement comprises one or more bundles whereby the second ends of a plurality of signal transmission conduits are collected in a bundle wherein the second ends of the transmission fibers in the bundle are in close proximity to each other.

5. The apparatus of claim 1, wherein said conduit reformatter comprises a reformatter frame comprising:
   an interface plate configured to secure the first ends of the respective signal transmission conduits in the first spatial arrangement;
   a base configured to secure the second ends of the respective signal transmission conduits in the second spatial arrangement; and
   and a side structure connecting the interface plate to the base at spaced-apart positions with respect to each other.

6. The apparatus of claim 5, further comprising heat dissipating fins extending from the interface plate.

7. The apparatus of claim 1, further comprising a signal coupling element operatively disposed with respect to the first end of each signal transmission conduit.

8. The apparatus of claim 1, wherein each of the receptacles is in optical communication with a single signal transmission conduit.

9. The apparatus of claim 1, wherein the processing module comprises an incubator.

10. The apparatus of claim 9, further comprising:
    an interface plate configured to secure the first ends of the respective signal transmission conduits in the first spatial arrangement, wherein the incubator is disposed on the interface plate; and
    heat dissipating fins extending from the interface plate.

11. The apparatus of claim 10, further comprising a fan to blow air across the heat dissipating fins.

12. The apparatus of claim 1, further comprising a plurality of receptacle holders within the processing module, wherein the first end of each signal transmission conduit is coupled to an associated one of the receptacle holders.

13. The apparatus of claim 1, further comprising one or more optical signal detectors, each optical signal detector being positioned or positionable with respect to the second ends of the respective signal transmission conduits and configured to emit an optical excitation signal that is transmitted from the second end of the transmission conduit to the first end of the transmission conduit and imparted to the contents of the associated receptacle and to receive an optical emission signal from the contents of the receptacle that is transmitted from the first end of the transmission conduit to the second end of the transmission conduit and convert the optical signal received to an electrical signal.

* * * * *